United States Patent [19]
Augustyns et al.

[11] Patent Number: 6,090,786
[45] Date of Patent: *Jul. 18, 2000

[54] SERINE PROTEASES, THEIR ACTIVITY AND THEIR SYNTHETIC INHIBITORS

[75] Inventors: Koen Jan Ludovicus Augustyns, Minderhout; Greta Constantia Vanhoof, Mortsel; Marianne Jean Frieda Borloo, Deurne; Ingrid Anna Jozef De Meester, Wilrijk; Filip Jozef Anny Goossens, Lokeren; Achiel Jean-Marie Haemers, Gent; Dirk Frans Hendriks, Aartselaar; Anne-Marie Virginie Renée Lambeir, Heverlee; Simon Lodewijk Scharpe, Wieze, all of Belgium

[73] Assignee: FondaTech Benelux N.V., Belgium

[*] Notice: This patent issued on a continued prosecution application filed under 37 CFR 1.53(d), and is subject to the twenty year patent term provisions of 35 U.S.C. 154(a)(2).

[21] Appl. No.: 08/750,484
[22] PCT Filed: Jun. 9, 1995
[86] PCT No.: PCT/EP95/02255
  § 371 Date: Feb. 19, 1997
  § 102(e) Date: Feb. 19, 1997
[87] PCT Pub. No.: WO95/34538
  PCT Pub. Date: Dec. 21, 1995

[30] Foreign Application Priority Data

Jun. 10, 1994 [EP] European Pat. Off. ............. 94201668
Dec. 20, 1994 [EP] European Pat. Off. ............. 94203707

[51] Int. Cl.$^7$ ............................ A61K 38/05; C07K 5/078
[52] U.S. Cl. .................... 514/19; 514/20; 514/2; 530/330; 540/130
[58] Field of Search .................. 514/19, 20, 2; 530/330; 540/130

[56] References Cited

U.S. PATENT DOCUMENTS

| | | | |
|---|---|---|---|
| 5,543,396 | 8/1996 | Powers et al. | 514/19 |
| 5,681,821 | 10/1997 | Powers et al. | 514/19 |
| 5,686,419 | 11/1997 | Powers et al. | 514/18 |

OTHER PUBLICATIONS

Belyaer et al, Tetrahedron Letters, vol. 36, (21), pp. 3755–3758, (1995).
Eltze, Arzheim–Forsch./Drug Res., 30 (II), No. 7, pp. 1129–1134, (1980).
Harada et al, Biochimica Biophysica Acta, vol. 705, pp. 288–290, (1982).
Uchin, et al, Int. J. Peptide Protein Res., vol. 34, pp. 33–36 (1989).

*Primary Examiner*—Keith D. MacMillan
*Assistant Examiner*—T. D. Wessendorf
*Attorney, Agent, or Firm*—Webb Ziesenheim Logsdon Orkin & Hanson, P.C.

[57] ABSTRACT

The present invention relates to new compounds of the general formula: Z-Xaa-Y', in which Xaa is an amino acid, Z is a protecting group and Y' is one of various types of ring structures. The new compounds have a modulating activity on serine proteases. The invention further relates to the use of the compounds in therapy and diagnosis and to a method of purifying the serine protease DPPIV.

4 Claims, 5 Drawing Sheets

SERINE PROTEASES, THEIR ACTIVITY AND THEIR SYNTHETIC INHIBITORS

BACKGROUND OF THE INVENTION

The present invention lies in the field of serine proteases, in particular serine proteases cleaving a post proline bond, such as the exopeptidase dipeptidyl peptidase IV (DPPIV) and the endopeptidase prolyl oligopeptidase (PO or PEP).

The invention relates to synthetic inhibitors of PEP and dipeptidyl peptidase IV, methods of their preparation and their therapeutic and diagnostic use.

Many biologically important peptide sequences contain proline. It confers unique conformational constraints on the peptide chain because the α-nitrogen atom of proline is part of the rigid pyrrolidine ring and, at the same time, is covalently bound by means of a secondary amide bond to the N-terminal preceding amino acid. Thus, the side-chain is cyclized back on to the backbone amide position. Inside an α-helix the possibility of making hydrogen bonds to the preceding turn is thereby lost and a kink will be introduced in the helix. The conformational restrictions imposed by proline motifs in a peptide chain probably implicate important structural or biological functions since a high degree of conservation is bound in many proteins and peptides.

An endo or C-terminal Pro-Pro bond and an endo pre-Pro peptide bond possess a high degree of resistance to any mammalian proteolytic enzyme. Only a limited number of peptidases are known to be able to hydrolyse proline adjacent bonds. Their activity is restricted by the isomeric state and the position of proline in the peptide chain. Dipeptidyl peptidase IV (DPPIV, also commonly referred to as CD26) is one of these peptidases. It is a serine protease which specifically cleaves N-terminal dipeptides from proteins and polypeptides carrying an unsubstituted N-terminus and a penultimate proline (or alanine) residue in trans conformation. DPPIV is a homodimer with subunit molecular weight of 110 kDa. It is a membrane protein expressed on the surface of lymphoid cells, epithelial and endothelial cells. Surface expression is increased significantly by T-cell activation. DPPIV has been reported to play a role in numerous processes such as T-cell costimulation, binding to proteins of the extracellular matrix, attachment of cancer cells to endothelium, binding to plasma adenosine deaminase, cooperation with entry of human immunodeficiency virus (HIV) into lymphoid cells.

The proteolytic activity of DPPIV resides in a stretch of approximately 200 amino acids located at the C-terminal end of the protein. The catalytic residues (Ser-629, Asp-708, His-740) are arranged in a unique order which is different from the classical serine proteases such as chymotrypsin and subtilisin. Proline specific dipeptidyl peptidase activity alters the biological activity of a large number of bioactive proteins and polypeptides comprising, amongst others, the neurotransmitter substance P, human growth hormone-releasing factor, erythropoietin, interleukin 2 and many others. Since many of these peptides have important effector functions, abnormal DPPIV activity—either too low or too high—will be reflected in an abnormal biological effect. Potential DPPIV substrates are listed in tables 1 and 2. The skilled person will easily recognize that interference with the effector function of these polypeptides may result in clinical conditions including inflammation, vascular diseases, auto-immune disease, multiple sclerosis, joint diseases and diseases associated with benign and malign cell transformation.

TABLE 1

Human cytokines, growth factors, neuro- and vasoactive peptides with a penultimate proline, which are putative substrates for DPP IV

| Polypeptide | N-terminal sequence |
|---|---|
| Interleukin-1β | Ala-Pro-Val-Arg-Ser- |
| Interleukin-2 | Ala-Pro-Thr-Ser-Ser- |
| Interleukin-5 | Ile-Pro-Thr-Glu-Ile- |
| Interleukin-6 | Val-Pro-Pro-Gly-Glu- |
| Interleukin-10 | Ser-Pro-Gly-Gln-Gly- |
| Interleukin-13 (recombinant) | Ser-Pro-Gly-Pro-Val- |
| Complement C4a | Lys-Pro-Arg-Leu-Leu- |
| Granulocyte chemotactic protein II | Gly-Pro-Val-Ser-Ala- |
| Granulocyte macrophage colony stimulating factor | Ala-Pro-Ala-Arg-Ser- |
| Granulocyte colony stimulating factor | Thr-Pro-Leu-Gly-Pro |
| Erythropoietin | Ala-Pro-Pro-Arg-Leu- |
| Gastrin releasing peptide | |
| Growth hormone | Phe-Pro-Thr-Ile-Pro- |
| Interferon inducible peptide 10 (γIP10) | Val-Pro-Leu-Ser-Arg- |
| Interferon regulatory factor 1 (IRF-1) | |
| Interferon regulatory factor 2 (IRF-2) | |
| Insulin-like growth factor-1 | Gly-Pro-Glu-Thr-Leu- |
| Melanoma growth stimulating activity | Ala-Pro-Leu-Ala-Thr- |
| Migration inhibition factor | Met-Pro-Met-Phe-Ile- |
| Monocyte chemotactic protein I | Glu-Pro-Asp-Ala-Ile- |
| Neuropeptide Y | Tyr-Pro-Ser-Lys-Pro- |
| Pancreatic polypeptide | Ala-Pro-Leu-Glu-Pro- |
| Peptide YY | Try-Pro-Ile-Lys-Pro- |
| Prolactin | Leu-Pro-Ile-Cys-Pro- |
| RANTES | Ser-Pro-Tyr-Ser-Ser- |
| Substance P* | Arg-Pro-Lys-Pro-Gln- |
| Thrombopoietin | Ser-Pro-Ala-Pro-Pro- |
| Transforming protein (N-myc) version 1 | Met-Pro-Gly-Met-Ile- |
| Transforming protein (N-myc) version 2 | Met-Pro-Ser-Cys-Ser- |
| Tumor necrosis factor β | Leu-Pro-Gly-Val-Leu- |
| Vascular endothelial growth factor | Ala-Pro-Met-Ala-Glu- |

*hydrolysis by DPP IV has already been proven (4, 5).

TABLE 2

Human peptides and proteins with a penultimate alanine, which are putative substrates for DPP IV

| Polypeptide |
|---|
| adenosine deaminase |
| annexins |
| breast basic conserved protein |
| cofilin |
| natural killer cell enhancing factor b |
| precursors of interferon α |
| precursors of interleukin 1-α and β, and interleukin 13 |
| precursors of macrophage inflammatory protein-2-α and β |
| precursor of melanocyte stimulating hormone |
| precursor of oxytocin-neurophysin 1 |
| Growth hormone releasing hormone* |
| β amyloid protein (1–28) |
| Anxiety peptide |
| 'joining peptide' of pro-opiomelanocortin |

*hydrolysis by DPP IV has already been proven (6).

DPPIV activity in serum is decreased in patients with auto-immune diseases and in patients receiving immuno-suppressant drugs (Hagihara, M., Ohhashi, M., Nagatsu, T. (1987) Clin. Chem. 33, 1463–1465; Doctoral thesis I. De Meester, 1992, "Characterization of Human Lymphocytic Dipeptidyl Peptidase IV and its identification as the Activation Antigen CD26", Universitaire Instelling Antwerpen, Departement Farmaceutische Wetenschappen.

Examples of auto-immune diseases are rheumatoid arthritis, systemic lupus erythematosus (this is a vascular disease), multiple sclerosis, Serum DPPIV activity is also decreased in malignancies such as gastrointestinal cancers (Haacke, W., Kullerts, G., & Barth, A. (1986) Arch.

Geschwulstforsch 56, 145–153) and blood cancers including acute lymphoid leukemia, lymphosarcoma and Hodgkin's disease (Kojima, J., Ueno, Y., Kasugai, H., Okuda, S., & Akedo, H. (1987) Clin. Chim. Acta 167, 285–291; Fujita, K., Hirano, M., Tokunaga, K., Nagatsu, T., & Sakakibara, S. (1977>) Clin. Chim. Acta 81, 215–217). DPPTV activity is increased in patients with hepatobiliary disease and hepatic cancer (Burchardt, U., Klagge, M., Hafstein, M., Salka, S., Graupner, H., Lenski, K., Delev, B., Neubert, K. & Barth, A. (1987) Z. Klin. Med. 42, 245–249). A role in inflammation can also be inferred from the observation that DPPIV is involved in costimulation and proliferation of granulocytes and macrophages (Bristol, L. A., Sakaguchi, K., Appella, E., Doyle, D., & Takacs, L. (1992) J. Immunol. 149, 367–372).

Also the response of T-lymphocytes to recall antigen and the entry of HIV have been reported to be at least partially influenced by the catalytic site of DPPIV. Recall antigen can be defined as an antigen that activates the immunological memory. It is an antigen to which the individual has been exposed before and which has previously triggered an immunological response. Tanaka et al. (Proc. Natl. Acad. Sci. USA 90, 4586–4590 (1993)) demonstrated that the active site of DPPIV is involved in the response to recall antigen. Callebaut et al. (Science 262, 2045–2046 (1993)) found an effect of catalytic site ligands in their model of HIV entry.

Prolyl endopeptidase (PEP), also called proline oligopeptidase (PO), was first discovered by Walter and coworkers as an oxytocin-degrading enzyme in the human uterus (Walter et al., Science 173, 827–829 (1971)). The enzyme cleaves peptide bonds at the carboxy-side of proline in peptides containing the sequence X-Pro-Y, where X is a peptide or N-terminal substituted amino-acid and Y is a peptide, amino acid, amide or alcohol (Yoshimoto et al., J. Biol. Chem. 253, 3708–3716 (1979)). The enzyme has a high specificity for the trans-conformation of the peptide bond at the imino-side of proline (Lin & Brandts, Biochemistry 22, 4480–4485 (1983)).

Prolyl endopeptidase has been characterized and purified form plants, micro-organisms and various mammalian sources. The enzyme is widely distributed among different mammalian tissues and high activity is found in brain, kidney, lung and muscle. The human enzyme has been purified from lung, brain, erythrocytes and placenta (Kalwant & Porter, Biochem. J. 276, 237–244 (1992)).

The sequences of prolyl oligopeptidase from *A. hydrophila* (Kanatani et al., J. Biochem. 113, 790–796 (1993)), *F. meningosepticum* (Yoshimoto et al., Agric. Biol. Chem. 55, 37–43 (1991)), porcine brain (Rennex et al., Biochemistry 30, 2195–2203 (1991)) and human lymphocytes (Vanhoof et al., Gene 149, 363–366 (1994)) have been determined.

In vitro PEP catalyzes the cleavage of several biologically active peptides such as angiotensin II, oxytocin, vasopressin, bradykinin. In vivo however its function remains obscure (Welches et al., Life Sci. 52, 1461–1480 (1993)). Recently it was shown that the prolyl oligopeptidase activity in plasma correlates well with the different stages of depression. Maes et al. (Biological Psychiatry 30, 577–586 (1991)) showed that DPPIV is decreased in major depression. It was proven to be the best biochemical marker for depression found so far.

Hydrolysis of angiotensin I and angiotensin II by prolyl oligopeptidase results in the liberation of angiotensin (1–7). Angiotensin (1–7) has vasodilator activity and modulates the release of vasopressin, which is able to influence the process of memory as was shown by injecting rats with specific PEP-inhibitors. The injection reverses the scopolamine induced amnesia. This experiment is not only an example which provides evidence for a possible physiologic function for the enzyme, but moreover it has led to the hypothesis that inhibitors for PEP can influence the memory process and counter dementia (Yoshimoto et al., J. Pharmacobio-Dyn. 10, 730–735 (1987); Furukawa et al., J. Pharmacobio-Dyn 12, S136 (1989)).

PEP may also be involved in the regulation of the blood pressure by participating in the renin-angiotensin system. PEP can decrease the amount of angiotensin II and its precursor and moreover the peptide generated by cleavage by PEP, angiotensin (1–7) itself has vasodilator activity (Kohara et al., Hypertension 17, 131–138 (1991)). Furthermore, involvement of PEP in vascular disease can be inferred from its ability to cleave bradykinin (which controls blood pressure) and blood coagulation factor X.

As indicated above, the proline specific serine proteases probably have a role in various physiological processes in the human and animal body, which processes might be related to various disease states, both physical and mental.

It is an object of the invention to interfere in the physiological action of proline specific serine proteases, such as PEP and DPPIV, to be able to treat the said disease states.

SUMMARY OF THE INVENTION

It is a further object of the invention to provide a tool for diagnosing such disease states.

According to a first aspect the invention therefore provides compounds according to claim 1, which compounds are able to inhibit the enzymatic activity of serine proteases, such as PEP and DPPIV. The compounds have the general formula:

Z-Xaa-Y' wherein

Z may or may not be present and represents a protecting group, such as benzyloxycarbonyl;

Xaa represents:
alanine, methionine, arginine, phenylalanine, aspartic acid, proline, asparagine, serine, cysteinie, threonine, glycine, tyrosine, glutamic acid, tryptophan, glutamine, valine, isoleucine, lysine, leucine, L-thioproline, L-homoproline, L-1,2,3,4, tetrahydroisoquinoline-3-carboxylic acid (Tic), L-2, 3-dihydroindol-2-carboxylic acid, L-naphthylglycine, L-phenylglycine, L-4-phenylproline, O-benzyl tyrosine, omega-Z lysine, omega-acetyl lysine;

and Y' represents:
a) a pyrrolidide of the general formula:

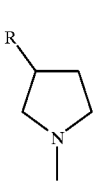

(II)

wherein R is a halogen atom, such as Cl, F, or =O; or b) phosphonate or phosphinate derivatives of the general formula

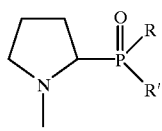

(III)

wherein R is phenyl, O-phenyl, R' is hydrogen, ($C_1$–$C_4$) alkyl, phenyl, benzyl, O-phenyl;
and wherein phenyl may be substituted; or
c) reduced peptides of the general formula:

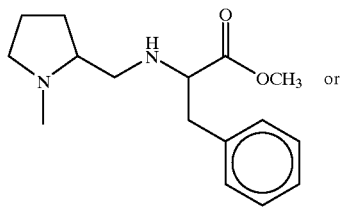

(V)

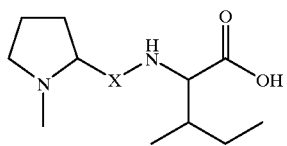

(VI)

wherein X is $CH_2$ or $CHOH$—$CH_2$;
or pharmaceutrically acceptable salts thereof.

The modulating compounds and the isolated enzymes may be used in various therapeutical and diagnostic applications as follows.

The modulators (inhibitors) may be used in pharmacotherapy of disease states related to inflammation, dysfunction of the immune system, vascular disease and proliferation disorders, for artificial induction of a state of immunosuppression, or in pharmacotherapy of neurological diseases. Diagnostic applications relate to imaging (wherein the inhibitors may be optionally labelled) and in vitro and in vivo diagnostic function tests.

The isolated enzyme may for example be used to enhance the activity of the endogenous enzyme, for example in immune stimulation as further described hereinbelow.

DESCRIPTION OF THE PREFERRED EMBODIMENTS

Figure 1:
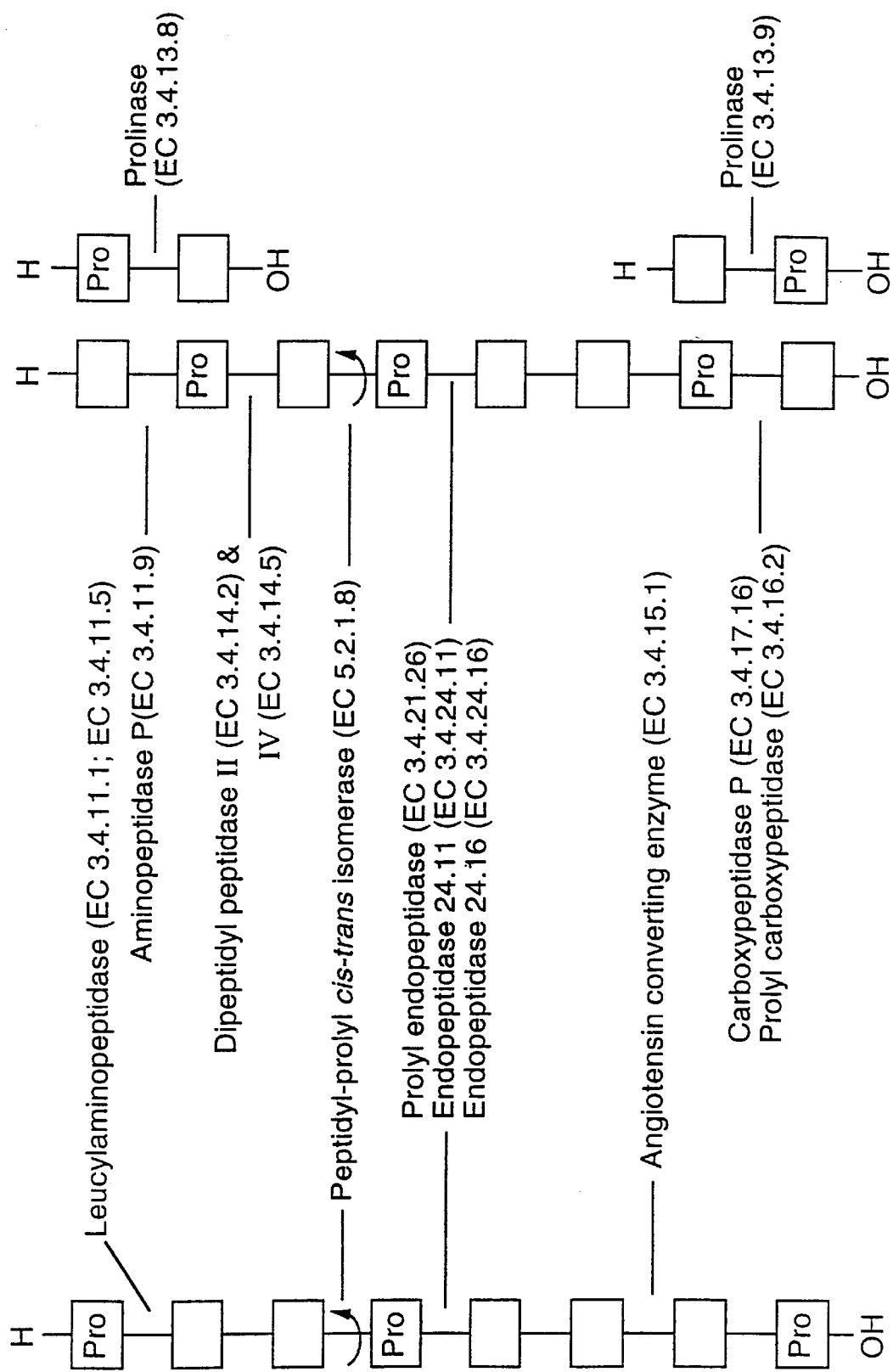
FIG. 1 shows a schematic representation of specificity of proline cleaving enzymes.

Hereinbelow the invention will be described in more detail. The Examples disclose the synthesis of the modulating compounds of the invention, the inhibitory activity of the compounds of the invention on the catalytic activity of human dipeptidyl peptidase IV (CD26) and PEP and the new isolation method of DPPIV and PEP.

In this application the terms "inhibitor", "compound", "derivative" and "modulating compound" are used interchangeably. Although the compounds will mostly have inhibiting properties they may in some situations have enhancing properties.

The synthetic inhibitors of the present invention are derived from dipeptides. The carboxylate group of the C-terminal amino acid is replaced by a hydrogen atom or a functional group mimicking the transition state of the enzyme or capable of specific modification of the active site. The C-terminal amino acid is proline, homoproline, azetidine, hydroxyproline or another substituted proline homolog. The N-terminal amino acid can be any naturally occurring amino acid or an amino acid which does not occur in nature, preferably with an aliphatic or aromatic side chains or proline. Examples of naturally occurring amino acids with aliphatic or aromatic side chains are leucine, isoleucine, valine, alanine, phenylalanine, tyrosine, tryptophan. Examples of amino acids which do not occur in nature are the D-isomers of the compounds mentioned before, synthetic amino acids with prostethic groups such as cyclohexylalanine, 1-naphthylalanine, p-fluoro-phenylalanine, O-tbutyl-tyrosine. Examples of the C-terminal substituent group are phosphonate esters, phosphinates or a hydrogen atom.

The present invention also includes derivatives which have been modified in the N-terminal amino acid side chain without abolishing the reactivity with the active site. Examples of such modifications are the incorporation of a radioactive label such as Iodine[125] into tyrosine, extension of the side chain to attach biotin or a fluorophore. To improve the half-life in the circulation the peptide bond between the two amino acids may be replaced by a non-hydrolyzable bond. The incorporation of a radioactive label is useful in diagnostic methods using the modulating compounds.

The compounds of the invention may be divider in a group in which the amino terminus is protected and a group of compounds which are not protected. The first group is particularly useful for inhibiting the activity of PEP, whereas the second type of compounds is specific for DPPIV. The protecting group may be any suitable group and its selection is within the scope of the skilled person in the field. A suitable protecting group is the benzyloxycarbonyl (Cbz) group.

Preferred compounds of this invention contain the diphenyl-phosphonate group (indicated with the symbol $^P(OPh)_2$). Substituted phenyl esters can also be used, for example p-chloro-phenyl esters or p-benzoic acid esters and their derivatives. The most preferred compounds of this type are: Pro-Pro$^P$-(OPh)$_2$, Phe-Pro$^P$-(OPh)$_2$, Ile-Pro$^P$-(OPh)$_2$, O-tButyl-Tyr-Pro$^P$-(OPh)$_2$, para-Fluoro-Phe-Pro-$^P$(OPh)$_2$, cyclohexylalanine-Pro-$^P$(OPh)$_2$, Ala-Pro-$^P$(OPh)$_2$, Arg-Pro$^P$-(OPh)$_2$, 1-naphthyl-Ala-Pro$^P$-(OPH)$_2$.

In another embodiment the compounds comprise a pyrollidine ring, that may optionally be substituted with a halogen. Of these compounds Ile-3-Fluoro-pyrrolidine is a particularly active inhibitor for DPPIV and Z-Pro-3-Fluoropyrrolidine for PEP.

A general description of the synthesis of the phosphonates is given below.

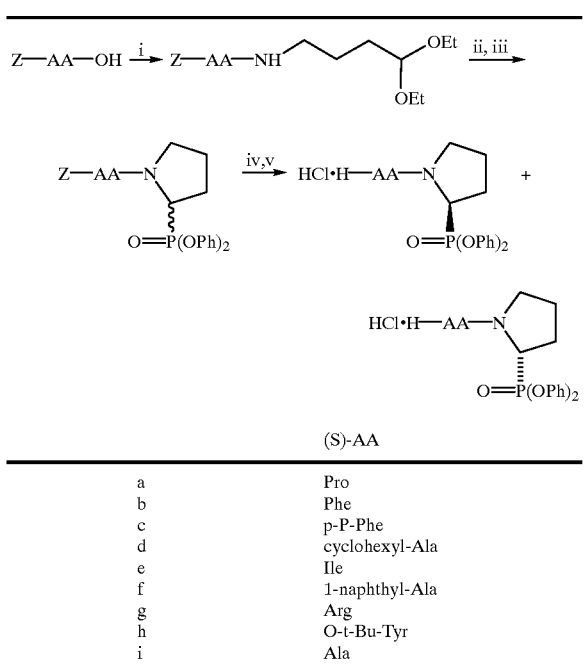

| | (S)-AA |
|---|---|
| a | Pro |
| b | Phe |
| c | p-P-Phe |
| d | cyclohexyl-Ala |
| e | Ile |
| f | 1-naphthyl-Ala |
| g | Arg |
| h | O-t-Bu-Tyr |
| i | Ala | i Method A: i-BuOCOCl, Et$_3$N, 4-ABAD, CHCl$_3$, −10° C., r.t. Method B: pentafluorophenol, DCC, 4-ABAD, CHCl$_3$, 0° C., r.t.

ii 0.5N HCl/THF, r.t., 1 h.

iii P(OPh)$_3$, AcOH, 80–85° C., 1 h.

iv H$_2$/Pd/C, MeOH/AcOH, r.t., 3–4 h.

v vacuum column chromatography: CHCl$_3$:MeoH:AcOH (25:1:1) 0.5N HCl/EtAc

The benzyloxycarbonyl (Cbz- or Z-)protected amino acids were coupled to 4-aminobutyraldehyde diethyl acetal (4-ABAD) using the standard mixed anhydride method (Bodanski, M. & A. Bodaneki, in: The Practice of Peptide Synthesis, Springer Verlag, Berlin, p.103–111 (1984)) (isobutylchloroformate, triethylamine) or through the pentafluorophfenol ester (DCC). The diethyl acetals were hydrolysed with 0.5N HCl in tetrahydrofuran (THF) (Matsuda F. et al.; Tetrahedron 41, 3625 (1985)) and the resulting mixture was treated with triphenylphosphite and acetic acid for one hour at 80–85° C. The cyclization of the acetal to pyrrolidine-2-phosphonate was based upon a method of Oleksyszyn and coworkers, (Synthesis, 985–986 (1979)). The obtained mixture of diastereoisomers were separated by vacuum chromatography. Deprotection of these products was performed by hydrogenolysis with hydrogen-palladium. Details of the synthesis and physicochemical properties of the compounds are given in Example 1. The evaluation of the inhibitory activity of the compounds is the subject of Example 2.

The ability of DPPIV/CD26 to specifically form a stable complex with adenosine deaminase was exploited in the purification method for DPPIV. Adenosine deaminase is coupled to a suitable matrix, for example dextran beads, latex, plastic or glass. DPPIV binds to the matrix. Unbound material is removed and DPPIV is eluted with a gentle washing procedure. A specific procedure using ADA coupled to cyanogen bromide activated Sepharose 4B is described in Example 5.

Because of the high specificity of the interaction between ADA and DPPIV a method such as described in Example 5 can also be used to purify DPPIV from complex mixtures such as biological fluids, tissue extracts or cell culture extracts used for expression of recombinant forms of DPPIV. Apart from the naturally occurring mammalian DPPIV, recombinant full-length protein, mutated forms with altered enzymatic activity, altered glycosylation patterns or truncated forms may be purified with this method as long as the ADA binding site remains intact. The same applies for DPPIV which has been chemically modified, for example linked to a PEG tail to improve the half life in the circulation, isotopically labelled or linked to a reporter enzyme or a fluorophore.

It has been found that PEP may very well be isolated from peripheral blood mononuclear cells (PBMC) and thrombocytes. Up till now this source for PEP has not been disclosed. The isolation of PEP from PBMC is the subject of Example 7.

The compounds described above can be used for the therapy of pathological states associated with excessive, impaired or unbalanced DPPIV or PEP activity.

Such clinical conditions may for example arise from the role of DPPIV in the function of the immunological memory, for example in autoimmune disease and foreign tissue rejection after transplantation (Fleisher, B., Immunology Today 15, 180–184 (1994); Morimoto, C. & S. F. Schlossman, The Immunologist 2, 4–7 (1994)). In such cases the DPPIV inhibitors of this invention can be used as immuno-suppressants.

In other cases, such as infections, an increased immune response may be required which can be modulated by administration of purified DPPIV preparations (Tanaka, T. et al., Proc. Natl. Acad. Sci. USA 91, 3082–3086 (1994)).

Improper processing or inactivation of biological effector molecules carrying the N-terminal X-Pro or X-Ala motif (see Tables 1 and 2) may imply DPPIV activity in a range of clinical conditions comprising, for example, inflammation, vascular disease, autoimmune disease, multiple sclerosis, joint diseases, diseases associated with benign and malign cell transformations.

Starting from the available information on the correlation between DPPIV or PEP and various disease states the skilled person will be able to define therapeutical utilities for the inhibitory compounds of the invention.

The invention also relates to the diagnostic use of the compounds. Labeled inhibitors can be used essentially in the same type of applications as labeled monoclonal antibodies, e.g. fluorescence and radioassays, cytofluorimetry, fluorescence activated cell sorting etc. The principles of such techniques can be found in immunochemistry handbooks, for example: A Johnstone and R. Thorpe, Immunochemistry in practice, 2nd. Ed. (1987), blackwell Scientific publications, Oxford London Edinburgh Boston Palo Alto Melbourne.

In cytochemistry and histochemistry labeled inhibitors can be used to directly visualize the cellular distribution of the target protease (DPPIV or PEP). The label can be fluorescent for fluorescence microscopy, radioactive for autoradiography, or electron dense for electron microscopy. The target structures can be whole cells, cells fixed onto slides or sections through solid tissue. A useful modification of these techniques is to use an indirect ("sandwich") assay employing the specific high affinity interaction between biotin and avidin (reviewed in Methods in Enzymology, vol. 184, 1990).

For imaging of tumours expressing high amounts of the target protease (DPPIV or PEP), inhibitors labeled with a suitable isotope (e.g. $^{123}$I or $^{131}$I) can be injected and after clearing of the excess inhibitor from the circulation, the tumour can be visualized by radioscintigraphy. The principles of imaging are summarized by A. Bamias & A. A. Epenetos (1995) in: Monoclonal antibodies, production, engineering and clinical application (M. A. Ritter and M. M. Ladyman, eds.) Cambridge university press, Cambridge New York Melbourne, pp. 222–246.

Localisation of DPPIV by means of monoclonal antibody and by enzymatic activity was reported to be diagnostically useful and applicable to clinical material in the case of thyroid follicular tumours and thyroid papillary carcinoma (Kotani, T et al., Int. J. Exp. Path. 73, 215–222 (1992); Kotani, T. et al., J. Path. 168, 41–45 (1992)). In an analogous manner the compounds of the invention which form a stable adduct with DPPIV may be used as a tool for diagnosing certain disease states.

It has been shown that DPPIV expression is specifically downregulated during malignant transformation of melanocytes. DPPIV is expressed on the surface of normal melanocytes but not on malignant melanoma cells (Morrison, M. E., Vijayaradhi, S., Engelstein, D., Albino, A. P. & Houghton, A. N. (1993) J. Exp. Med. 177, 1135–1143). According to the invention specific cytochemical or histochemical localisation of DPPIV can be used to diagnose malignancy in melanoma cells.

The present invention furthermore relates to the use of the inhibitory compounds in various therapeutical applications. In order to demonstrate the usefulness of these compounds in therapy some experiments have been performed showing in vivo inhibitory activity of the compounds on both DPPIV and PEP. Example 4 shows the DPPIV catalyzed degradation of vasostatin and inhibition thereof, whereas Example 9 relates to the activity of PEP on bradykinin and substance P, a neurotransmitter peptide with an aminoterminal X-Pro-motif and the inhibition thereof as a model for the potential therapeutic use of the inhibitors in medicin.

The present invention thus also encompasses pharmaceutical compositions prepared for storage and subsequent administration, which have a pharmaceutically effective amount of the compounds disclosed above in a pharmaceutically acceptable carrier or diluent. Acceptable carriers and diluents are well known and are described, for example, in Remington's Pharmaceutical Sciences, Mack Publishing Co. (A. R. Gennaro edit. 1985). Preservatives, stabilizers, dyes and flavoring agents may be provided in the pharmaceutical compositions. For example, sodium benzoate, sorbic acid and esters of p-hydroxybenzoic acid may be added as preservatives. In addition antioxidants and suspending agents may be used.

The compositions of this invention may be formulated and used as tablets, capsules or elixirs for oral administration; suppositories for rectal administration; sterile solutions or suspensions for injectable administration; aerosols; unguents for topical administration. If desired, absorption enhancing preparations (e.g. liposomes) or other appropriate delivery systems may be used. The amount of the active substances(s) in a dosage unit may vary between 0.01 mg and 1 g.

The compounds or compositions of this invention can be used alone or in combination with one another, or in combination with other therapeutic or diagnostic agents. The dosage for the compounds of the present invention can range broadly depending upon the desired effects and the therapeutic indication.

The DPPIV inhibitors described above which form covalent, long-lived adducts with DPPIV are therefore suitable for diagnostic applications such as imaging and histochemical staining of DPPIV. This requires the introduction of a radio-isotope, e.g. iodine, or a fluorescent or other type of reporter group. Because of their small size they are expected to penetrate tissue more easily as, for example, antibodies. Moreover it was found that they only recognize DPPIV which is native and enzymatically active. Formulations of the compounds to be used in diagnostic applications are also part of this invention.

DPPIV activity can interfere with other enzymatic assays by cleaving the substrate used in the test and thereby giving either false positive (when a chromogenic substrate is cleaved) or false negative results (when a peptide substrate is degraded). The inhibitors of this invention can be used to inactivate contaminating DPPIV before carrying on with the analysis. An example of this is the fluorogenic assay for proline specific endoprotease the substrate of which, Gly-Ala-4-Me-2-NA, is also cleaved by DPPIV. Another application can be found in the decontamination of aminopeptidase M preparations.

The DPPIV inhibitors can also be used to avoid degradation of bioactive peptides which contain an aminoterminal X-Pro-motif (e.g. cytokines) in biological samples prior to analysis.

The present invention will be further elucidated with reference to the following examples which are only given for illustration purposes and are in no way intended to limit the invention.

EXAMPLES

Example 1

Synthesis and Characterization of Modulating Compounds of the Invention

5 A. PHOSPONATES a) Materials and methods

The amino acids used in the synthesis were obtained from various manufacturers. (S)-alanine, (S)-isoleucine, (S)-phenylalanine, (S)-proline were purchased from Janssen Chimica NV; tri-Z-(S)-arginine, (S)-homoproline, Z-(S)-p-fluorophenylalanine, (S)-cyclohexylalanine, (S)-(1-naphtyl)alanine, (S)-1,2,3,4-tetrahydroisoquinoline-3-carboxylic acid [(S)-Tic] were purchased from Bachem AG.

Melting points were determined on a Digital Melting Point Apparatus (Electrothermal) and are uncorrected. $^1$H-NMR spectra were recorded on a Bruker (300 MHz) spectrometer. Observed rotations at the Na-D line were obtained at 20° C. using a Perkin-Elmer 241 polarimeter. Mass-spectra were recorded on a VG 70 SEQ (Fisons, VG analytical) spectrometer. TLC was carried out on plates precoated with silica gel Merck UV-254. Column chromatography was performed with silica gel H, 5–40 μm, purchased from Fluka, Aldrich, Sigma.

b) Synthesis of the intemediate (4-[(8)-2-benzyloxycarbonylaminoacyl] aminobutyraldehyde diethyl acetals Acetals are intermediates in the synthesis of were prepared by coupling the corresponding N-benzyloxycarbonyl (N-Cbz) protected amino acid with 4-aminobutyraldehyde diethyl acetal using the standard mixed anhydride method (supra) with isobutylchloroformate (Method A) or via pentafluorophenol ester without isolation of the latter (Method B). The following intermediates were prepared:

1. 4-(N-Cbz-(S)-alanyl)aminobutyraldehyde diethyl acetal: yield 65% (Method A), oil.
2. 4-(N-Cbz-(S)-isoleucyl)aminobutyraldehyde diethyl acetal:
    yield 77% (Method A), mp 135° C., $[\alpha]_D^{20}$=−5.5° (C1, CHCl$_3$).

3. 4-(N-Cbz-(S)-phenylalanyl) aminobutyraldehyde diethyl acetal:

yield 66% (Method A), mp 145° C., $[\alpha]_D^{20}$=6.0° (C1, CHCl$_3$).

4. 4-(N$^2$, N$^7$, N$^{7'}$-tri-Cbz-(S)-arginyl) aminobutyraldehyde diethyl acetal:

yield 99% (Method B), mp 158° C., $[\alpha]_D^{20}$=12.1° (C1, CHCl$_3$).

5. 4-(N-Cbz-(S)-prolyl)aminobutyraldehyde diethyl acetal:

yield 92% (Method B, purified by the vacuum column chromatography), mp 67° C., $[\alpha]_D^{20}$=−68.7° (C1, CHCl3).

6. 4-(N-Cbz-(S)-homoprolyl) aminobutyraldehyde diethyl acetal:

yield 93% (Method B, purified by the vacuum column chromatography), oil, $[\alpha]_D^{20}$=−48.4° (C1, CHCl$_3$).

7. 4-(N-Cbz-(S)-p-fluoraphenylalanyl) aminobutyraldehyde diethyl acetal:

yield 99% (Method B), mp 143° C., $[\alpha]_D^{20}$=2.8° (C1, CHCl$_3$).

8. 4-[N-Cbz-(S)-(1-nalphtyl) alanyl]aminobutyraldehyde diethyl acetal:

yield 81% (Method B, purified by the vacuum column chromatography), mp 112° C.

9. 4-(N-Cbz-(S)-cyclohexylalanyl)aminobutyraldehyde diethyl acetal:

yield 81% (Method B, purified by the vacuum column chromatography), mp 102° C., $[\alpha]_D^{20}$=−13.3° (C1, CHCl$_3$).

10. 4-[(N-Cbz-(S)-tetrahydroisoquioline)-3-carbonyl] aminobutyraldehyde diethyl acetal:

yield 75% (Method B, purified by the vacuum column chromatography), oil, $[\alpha]_D^{20}$=−2.1° (C1, CHCl$_3$).

c) Synthesis of diphonyl 1-[(S)-2-benzyloxycarbonyl-amino-acyl] pyrrolidin-2-phosphonates (General procedure for protected phosphonates)

0.5 N aqueous HCl Solution (30 ml, 15 mmole) was added at room temperature to the solution of diethyl acetal (10 mmole) in THF (60 ml). The mixture was stirred for 1 h. After the addition of ether (85 ml), the pH of the mixture was adjusted to 7–8 with 1N NaOH. The organic layer was separated and the aqueous layer was washed with ether (60 ml). The combined organic layer was dried (MgSO$_4$) and evaporated to dryness under reduced pressure. The resulting oil was dissolved in acetic acid (30 ml), triphenylphosphite [P(OPh)$_3$] (20 mmole) was added and the solution was stirred at 80–85° C. for 1 h. The mixture was cooled and evaporated at 45–50° C. under reduced pressure. The residue was dissolved in chloroform (50 ml). The solution was washed with water, saturated NaHCO$_3$ solution, dried (MgSO$_4$) and evaporated to dryness under reduced pressure. The crude compound was purified on a vacuum column using ethyl acetate—petroleum ether (1:1 or 1:2) as mobile phase. The following compounds were prepared:

11. Diphenyl 1-(N-Cbz-(S)-alanyl) pyrrolidine-2-phosphonate:

yield 65%, oil. $^1$N-NMR (CDCl$_3$/TMS): 1.35 (dd, 3H), 1.8–2.7 (m, 4H), 3.3–3.9 (m, 2H), 4.1 (m, 1H), 4.45 (m, 1H), 5.1 (m, 2H), 5.8 (m, 1H), 7.0–7.4 (m, 15H).

12. Diphenyl 1-(N-Cbz-(S)-isoleucyl)pyrrolidine-2-phosphonate:

yield 66%, oil. $^1$H-NMR (CDCl$_3$/TMS): 0.8 (t, 3H), 1.0 (d, 3H), 1.25 (m, 1H), 1.55 (m, 1H), 1.9–2.8 (m, 4H), 3.4–3.9 (m, 2H), 4.4 (m, 1H), 5.1 (m, 2H), 5.5 (m, 2H), 7.0–7.4 (m, 15H).

13. Diphenyl 1-(N-Cbz-(S)-phenylalanyl)pyrrolidine-2-phosphonate:

yield 74%, semicrystalline oil. $^1$H-NMR (CDCl$_3$/TMS): 1.3–2.7 (m, 4H), 2.8–3.6 (m, 4H), 4.7 (m, 1H), 5.0 (m, 1H), 5.1 (m, 2H), 5.35 (m, 1H), 7.0–7.4 (m, 20H). MS (FAB) m/e (rel. intensity): 585 (M+H)$^+$ (100).

14. Diphenyl 1-(N$^2$,N$^7$,N$^{7'}$-tri-Cbz-(S)-arginyl)pyrrolidine-2-phosphonate:

yield 40%, oil. $^1$H-NMR (CDCl$_3$/TMS):

15. Diphenyl 1-(N-Cbz-(S)-prolyl)pyrrolidine-2-phosphonate:

yield 66%, oil. $^1$H-NMR (CDCl$_3$/TMS): 1.5–2.8 (m, 8H), 3.2–4.0 (m, 4H), 4.6 (m, 1H), 4.85 (m, 1H), 5.1 (m, 2H), 7.0–7.5 (m, 15H).

16. Diphenyl 1-(N-Cbz-(S)-homoprolyl)pyrrolidine-2-phosphonate:

yield 54%, semicrystalline oil. $^1$H-NMR (CDCl$_3$/TMS):

17. Diphenyl 1-(N-Cbz-(S)-p-fluorophenylalanyl) pyrrolidine-2-phosphonate:

yield 70%, oil. $^1$H-NMR (CDCl$_3$/TMS): 1.2–2.8 (m, 4H), 2.9–4.0 (m, 4H), 4.6 (m, 1H), 4.8 (m, 1H), 5.05 (m, 2H), 5.6 (m, 1H), 6.5–7.5 (m, 19H).

18. Diphenyl 1-(N-Cbz-(S)-cyclohexylalanyl) pyrrolidine-2-phosphonate:

yield 55%, semi-crystalline oil. $^1$H-NMR (CDCl$_3$/TMS): 0.6–2.5 (m, 17H), 3.75 (m, 2H), 4.6 (m, 1H), 5.0 (m, 3H), 5.35 (m, 1H), 7.0–7.4 (m, 15 H).

19. Diphenyl 1-[N-Cbz-(S)-(1-naphthyl) alanyl]pyrrolidine-2-phosphonate:

yield 68%, semicrystalline oil. $^1$H-NMR (CDCl$_3$/TMS): 1.0–2.4 (m, 4H), 2.8–4.0 (m, 4H), 5.1 (m, 3H), 5.35 (m, 1H), 6.05 (m, 1H), 6.9–8.5 (m, 22H).

20. Diphenyl 1-[(N-Cbz-(S)-tetrahydroisoquinolyl)-3-carbonyl]pyrrolidine-2-phosphonate:

yield 76%, semicrystalline oil. $^1$H-NMR (CDCl$_3$/TMS): 1.5–2.5 (m, 4H), 2.9 (m, 3H), 3.45 (m, 2H), 3.75 (m, 1H), 4.0 (m, 1H), 4.5–5.3 (m, 3H), 6.9–7.5 (m, 19H).

d) Diphenyl (S)- and (R)-1-[(S)-aminoacyl]pyrrolidine-2-phosphonate hydrochlorides (General procedure for unprotected phosponates).

Method A

Z(or Cbz)-protected phosphonate (1 mmole) was dissolved in a mixture of methanol (20 ml) and acetic acid (0.5 ml). The solution was hydrogenated over 10% Pd/C at room temperature for 3–6 h (the reaction was monitored by TLC). The catalyst was removed on a celite filter and the filtrate was evaporated under reduced pressure. The residue was dissolved in dry CHCl$_3$, 0.5N HCl in EtOAc (2.5 ml) was added and the product was precipitated with ether or hexane-ether mixtures. The solid was collected and dried in a vacuum desiccator over NaOH. This procedure has been used when no separation of diastereomers could be detected on TLC.

Method B

Z-Protected-phosphonate was deblocked as above, but after removal of the catalyst and evaporation of the filtrate the residue was purified on a vacuum column with CHCl$_3$-MeOH-AcOH (25:1:1) as eluent. Fractions containing pure diastereomers were evaporated under reduced pressure, the residue was dissolved in dry CHCl$_3$, 0.5N HCl in EtOAc was added and the product was precipitated with ether or hexane-ether mixtures. The solid was collected and dried in the vacuum desiccator over NaOH.

Most of dipeptide phosphonate hydrochlorides obtained melted in a wide interval and (or) with decomposition and had no clear melting paint.

21. Diphenyl (S,R)-1-[(S)-alanyl]pyrrolidine-2-phosphonate hydrochloride:
    yield 60% (method A), hygroscopic solid.
22. Diphenyl (R)-1-[(S)-isoleucinyl]pyrrolidine-2-phosphonate hydochloride:
    yield 30% (method B), mp 199° C., $[\alpha]_D^{20}=-26.0°$ (C1, MeOH). $^1$H-NMR (CDCl$_3$/TMS): 0.75 (t, 3H), 1.0 (d, 3H), 1.25 (m, 1H), 1.55 (m, 1H), 1.8–2.7 (m, 5H), 3.3–4.0 (m, 2H), 4.05 (m, 1H), 5.05 (m, 1H), 7.0–7.4 (m, 10H), 8.35 (br s, 3H). MS (FAB) m/e (rel. intensity): 417 (M-C1)$^+$ (100).
23. Diphenyl (S,R)-1-[(S)-isoleucinyl]pyrrolidine-2-phosphonate hydochloride:
    35 yield 90% (method A), hygroscopic solid.
24. Diphenyl (S)-1-[(S)-phenaylalyl]pyrrolidine-2-phosphonate hydrochloride:
    yield 37% (method B), hygroscopic solid, $[\alpha]_D^{20}=103.3°$ (C1, MeOH). $^1$H-NMR (CDCl$_3$/TMS): 0.7–2.6 (m, 4H), 2.9–3.7 (m, 4H), 3.9 (m, 0.2H), 4.5 (m, 0.8H), 4.7 (m, 0.8H), 5.25 (m, 0.2H), 6.9–7.5 (m, 15H), 8.2 (br s, 0.6H), 8.8 (br s, 2.4H). MS (FAB) m/e (rel. intensity): 451 (M-C1)$^+$ (100).
25. Diphenyl (R)-1-[(S)-phenylalanyl]pyrrolidine-2-phosphonate hydrochloride:
    yield 25% (method B), hygroscopic solid, $[\alpha]_D^{20}=5.5°$ (C1, MeOH). $^1$H-NMR (CDCl$_3$/TMS): 1.7–2.6 (m, 4H), 3.1–3.8 (m, 4H), 4.4 (m, 1H), 5.05 (m, 1H), 6.8–7.5 (m, 15H), 8.7 (br s, 3H). MS (FAB) m/e (rel. intensity): 451 (M-C1)$^+$ (100).
26. Diphenyl (S,R)-1-[(S)-arginyl]pyrrolidine-2-phosphonate dihydrochloride:
    yield 60% (method A), hygroscopic solid.
27. Diphenyl (S,R)-1-[(S)-prolyl]pyrrolidine-2-phophonate hydrochloride:
    yield 79% (method A), hygroscopic solid. $^1$H-NMR (CDCl$_3$/TMS): 1.5–2.7 (m, 8H), 3.0–4.0 (m, 4H), 6.3 (m, 1H), 7.9–8.5 (m, 1H).
28. Diphenyl (S)-1-[(S)-homoprolyl]pyrrolidine-2-phosphonate hydrochloride:
    yield 43% (method B), hypgroscopic solid, $[\alpha]_D^{20}=48.3°$ (C1, CHCl$_3$).
29. Diphenyl (R)-1-[(S)-homoprolyl]pyrrolidine-2-phosphonate hydrochloride:
    yield 40% (method B), hygroscopic solid, $[\alpha]_D^{20}=-45.3°$ (C1, CHCl$_3$).
30. Diphenyl (S)-1-[(S)-p-fluorophenylalanyl]pyrrolidine-2-phosphonate hydrochloride:
    yield 20% (method B), hygroscopic solid, $[\alpha]_D^{20}=86.6°$ (C1, MeOH). $^1$H-NMR (CDCl$_3$/TMS): 0.8–2.7 (m, 4H), 2.8–3.7 (m, 4H), 3.9 (m, 0.25H), 4.55 (m, 0.75H), 4.7 (m, 0.75H), 5.25 (m, 0.25H), 6.5–7.5 (m, 14H), 8.3 (br s, 0.75H), 8.85 (br s, 2.25H).
31. Diphenyl (R)-1-[(S)-p-fluorophenylalanyl]pyrrolidine-2-phosphonate hydrochloride:
    yield 16% (method B), hygroscopic solid, $[\alpha]_D^{20}=-2.2°$ (C1, MeOH). $^1$H-NMR (CDCl$_3$-CD$_3$OD/TMS): 1.9–2.6 (m, 4H), 2.8–3.2 (m, 1H), 3.4–4.0 (m, 2H), 4.5 (m, 1H), 5.0 (m, 1H), 6.7–7.6 (m , 14H).
32. Diphenyl (S)-1-[(S)-cyclohexylalanyl]pyrrolidine-2-phosphonate hydrochloride:
    yield 47% (method B), hygroscopic solid, $[\alpha]_D^{20}=61.50°$ (C1, CHCl$_3$). $^1$H-NMR (CDCl$_3$/TMS): 0.5–2.7 (m, 17H), 3.2–4.1 (m, 2H), 4.1–4.6 (m, 1H), 4.2–5.3 (m, 1H), 6.7–7.5 (m, 10H), 8.36 (br s, 1H), 8.55 (br s, 2H).
33. Diphenyl (R)-1-[(S)-cyclohexylalanyl]pyrrolidine-2-phosphonate hydrochloride:
    yield 31% (method B), hygroscopic solid, $[\alpha]_D^{20}=-43.5°$ (C1, CHCl$_3$). $^1$NMR (CDCl$_3$/TMS): 0.5–3.0 (m, 17H), 3.1–4.1 (m, 2H), 4.3 (m, 1H), 5.35 (m, 1H), 6.7–7.5 (m, 10H), 8.5 (br s, 3H).
34. Diphenyl (S)-1-[(S)-(1-naphthyl)alanyl]pyrrolidine-2-phosphonate hydrochloride:
    yield 20% (method B), hygroscopic solid, $[\alpha]_D^{20}=-80.0°$ (C2, CHCl$_3$). $^1$H-NMR (CDCl$_3$/TMS): 0.5–2.1 (m, 4H), 3.15 (m, 2H), 3.4–4.1 (m, 2H), 4.4–4.6 (m, 2H), 6.7–8.2 (m, 17H), 9.05 (br s, 3H).
35. Diphenyl (R)-1-[(S)-(1-naphthyl)alanyl]pyrrolidine-2-phosphonate hydrochloride:
    yield 20% (method B), hygroscopic solid, $[\alpha]_D^{20}15.5°$ (C0.5, CHCl$_3$-MeOH 1:1). $^1$H-NMR (CDCl$_3$-CD$_3$OD/TMS): 0.6–2.5 (m, 4H), 2.7–3.1 (m, 2H), 3.2–4.0 (m, 2H), 4.8–5.0 (m, 2H), 6.7–8.3 (m, 17H).
36. Diphenyl (S)-1-[(S)-(tetrahydroisoquinolyl)-3-carbonyl]pyrrolidine-2-phosphonate hydro-chloride:
    yield 24% (method B), hygroscopic solid, $[\alpha]_D^{20}=51.8°$ (C1, CHCl$_3$). $^1$H-NMR (CDCl$_3$/TMS): 1.8–2.8 (m, 4H), 3.1–3.5 (m, 3H), 3.75 (m, 1H), 4.0–5.5 (m, 4H), 6.7–7.5 (m, 14H), 8.75 (br s, 2H).
37. Diphenyl (R)-1-[(S)-(tetrahydroisoquinolyl)-3-carbonyl]pyrrolidine-2-phosphonate hydro-chloride:
    yield 34% (method B), hygroscopic solid, $[\alpha]_D^{20}=-71.5°$ (C1, CHCl$_3$). $^1$H-NMR (CDCl$_3$-CD$_3$OD/TMS): 2.0–2.7 (m, 4H), 2.8–3.2 (m, 2H), 3.5–4.5 (m, 5H), 5.1 (m, 1H), 6.9–7.6 (m, 14H).

B. PYRROLIDINES

1. Z-pro-3-fluoro-pyrrolidine (PEP inhibitor)

The intermediate 1-[N-Benzyloxycarbonyl-L-propyl]-3(R,S)-hydroxypyrrolidine was prepared as follows. To a mixture of N-benzyloxycarbonyl-L-proline (1.25 g, 5 mmol), (R,S)-hydroxypyrrolidine (0,44 g, 5 mmol) and benzotriazol-1-yloxytris(dimethylamino)phosphonium hexafluorophosphonium hexafluorophosphate (2.21 g, 5 mmol) in dimethylformamide (20 ml) was added triethylamine (1.4 ml, 10 mmol). After stirring at room temperature overnight, water (100 ml) was added and the mixture was extracted with EtOAc (3×50 ml). The combined organic layer was washed with HCl (2N, 2×25 ml), water (25 ml), NaHCO$_3$ (5%, 2×25 ml) and brine (25 ml). The organic layer was dried, evaporated and purified by column chromatography [CH$_2$Cl$_2$; CH$_2$Cl$_2$-MeOH(98-2); CH$_2$Cl$_2$-MeOH(97-3); CH$_2$Cl$_2$-MeOH(96-4);CH$_2$Cl$_2$-MeOH(95-5)) yielding 0.56 g (1.76 mmol, 35%) of the intermediate compound as an oil. $^1$H NMR (CDCl$_3$) δ 1.70–2.00 (m, 3H, γ-CH$_2$, β-CH), 2.00–2.20 (m, 3H, β-CH, 4-CH$_2$), 3.15–3.95 (m, 6H, 2-CH$_2$, 5-CH$_2$, δ-CH$_2$), 4.15–4.55 (m, 2H, α-CH, 3-CH), 4.95–5.20 (m, 2H, CH$_2$C$_6$H$_5$), 7.20–7.35 (m, 5H, C$_6$H$_5$).

Subsequently 1-[N-Benzyloxycarbonyl-L-propyl]-3(R,S)-fluoropyrrolidine was prepared by treating a solution of 1-[N-Benzyloxycarbonyl-L-propyl]-3(R,S)-hydroxypyrrolidine (0.31 g, 0.97 mmol) in 1,2-dichloroethane dry (10 ml) with diethylaminosulfur trifluoride (0.26 ml, 1.94 mmol) at 0° C. under nitrogen. After stirring for 2 h the reaction mixture was poured in a NaHCO$_3$ solution (5%, 100 ml) and stirred for 15 min. This mixture was extracted with CH$_2$Cl$_2$ (2×100 ml) and the combined organic layer was dried, evaporated and purified by column chromatography [CH$_2$Cl$_2$; CH$_2$Cl$_2$-MeOH(99-1); CH$_2$Cl$_2$-MeOH(98-2)] yielding 0.21 g (0.66 mmol, 68%) of the compound as a solid. The compound was crystallized from EtOAc-hexane. $^1$H NMR (CDCl$_3$) δ 1.70–2.00 (m, 3H, γ-CH$_2$, β-CH), 2.00–2.45 (m, 3H, β-CH, 4-CH$_2$), 3.15–4.10 (m, 6H, 2-CH$_2$, 5-CH$_2$, δ-CH$_2$), 4.10–4.35 (m, 1H, α-CH, 3-CH), 4.90–5.45 (m, 3H, CH$_2$C$_6$H$_5$), 7.20–7.35 (m, 5H, C$_6$H$_5$).

2. Synthesis of Ile-3-fluoro-pyrrolidine (DPPIV inhibitor)

The intermediate 1-[N-tert-Butyloxycarbonyl)-L-isoleucyl]-3(R,S)-hydroxypyrrolidine was prepared as follows. To a mixture of N-(tert-butyloxycarbonyl)-L-isoleucine (6.94 g, 30 mmol), (R,S)-3-hydroxypyrrolidine (2.61 g, 30 mmol) and benzotriazol-1-yloxytris (dimethylamino)phosphonium hexafluorophosphate (14.6 g, 33 mmol) in dimethylformamide (60 ml) was added triethylamine (9.2 ml, 66 mmol). After stirring at room temperature overnight, water (300 ml) was added and the mixture was extracted with EtOAc (3×150 ml). The combined organic layer was washed with HCl (2N, 2×100 ml), water (100 ml), $NaHCO_3$ (5%, 2×100 ml) and brine (100 ml). The organic layer was dried, evaporated and purified by column chromatography [$CH_2Cl_2$; $CH_2Cl_2$-MeOH(98-2); $CH_2Cl_2$-MeOH(97-3); $CH_2Cl_2$-MeOH(96-4)] yielding 5.83 g (19.43 mmol, 65%) of the intermediate compound as a foam. $^1H$ NMR ($CDCl_3$) δ 0.89 (t, J=7.5 Hz, 3H, δ-$CH_3$,), 0.93 (d, J=6.6 Hz, 3H, γ-$CH_3$), 1.00–1.25 (m, 1H, γ-CH) 1.42 (s, 9H, $C(CH_3)_3$), 1.50–1.65 (m, 1H, γ-CH), 1.65–1.80 (m, 1H, β-CH), 1.90–2.15 (m, 2H, 4-$CH_2$), 3.40–4.15 (m, 4H, 2-$CH_2$, 5-$CH_2$), 4.15–4.35 (m, 1H, α-CH), 4.48 (br s, 1H, 3-CH) 5.33 (d, J=9.3 Hz) and 5.42 (d, J=9.9 Hz) (1H, NH).

Subsequently the protected compound 1-[N-(tert-Butyloxycarbonyl)-L-isoleucyl]-3 (R,S)-fluoropyrrolidine was prepared by treating a solution of 1-N-(tert-butyloxycarbonyl)-L-isoleucyl]-3(R,S)-hydroxypyrrolidine (0.40 g, 1.33 mmol) in 1,2-dichloroethane dry (15 ml) with diethylaminosulfur trifluoride (0.35 ml, 2.66 mol) at 0° C. under nitrogen. After stirring for 2 h the reaction mixture was poured in a $NaHCO_3$ solution (5%, 100 ml) and stirred for 15 min. This mixture was extracted with $CH_2Cl_2$ (2×100 ml) and the combined organic layer was dried, evaporated and purified by column chromatography [$CH_2Cl_2$; $CH_2Cl_2$-MeOH(99-1); $CH_2Cl_2$-MeOH(98-2)] yielding 0.27 g (0.89 mmol, 67%) of the compound as an oil. $^1H$ NMR ($CDCl_3$) δ 0.85–1.00 (m, 6H, δ-$CH_3$, γ-$CH_3$), 1.05–1.25 (m, 1H, γ-CH), 1.43 (s, 9H, $C(CH_3)_3$), 1.50–1.65 (m, 1H, γ-CH), 1.65–1.80 (m, 1H, β-CH), 1.90–2.45 (m, 2H, 4-$CH_2$), 3.40–4.10 (m, 4H, 2-$CH_2$, 5-$CH_2$), 4.10–4.40 (m, 1H, α-CH), 5.20–5.35 (m, 1H, NH), 5.28 (dm, J=52.2 Hz, 1H, 3-CH).

The DPPIV inhibitor 1-(L-Isoleucyl)-3(R,S)-fluoropyrrolidine trifluoroacetate was prepared by treating 1-[N-(tert-Butyloxycarbonyl)-L-isoleucyl]3(R,S)-fluoropyrrolidine (0.34 g, 1.13 mmol) with TFA (5 g) for 1 h at room temperature. The inhibitory compound was obtained in quantitative yield after evaporation, coevaporation with toluene (3 times) and MeOH (3 times). The compound was crystallized from MeOH-$Et_2O$. $^1H$ NMR (DMSO-$d_6$) δ 0.86 (t, J=7.2 Hz, 3H, δ-$CH_3$), 0.93 (m, 3H, γ-$CH_3$), 1.05–1.25 (m, 1H, γ-CH), 1.40–1.65 (m, 1H, γ-CH), 1.75–1.95 (m, 1H, β-CH), 2.00–2.30 (m, 2H, 4-$CH_2$), 3.35–4.10 (m, 5H, 2-$CH_2$, 5-$CH_2$, α-CH), 5.38 (dm, J=52.9 Hz, 1H, 3-CH), 8.18 (s, 3H, $NH_3^+$).

C. REDUCED PEPTIDES

The preparation of methyl (S,S)-3-aza-2-benzyl-4-(1-glycyl-2-pyrrolidinyl)butanoate and methyl (S,S,S)-3-aza-2-benzyl-4-(1-phenylalanyl-2-pyrrolidinyl)butanoate was performed as follows. To a solution of N-t-butyloxycarbonyl-(S)-prolinal (12.35 mmol, 2.46 g) in dry methanol (75 ml) were added at 0° C., 7.5 g molecular sieves (3Å, powder) and (S)-phenylalanine methylester hydrochloride (13.65 mmol, 2.94 g). Then sodium cyanoborohydride (13.65 mmol, 0.86 g) was added and the reaction mixture was stirred overnight at room temperature. After filtration of the sieves, the solvent was evaporated and the residue was taken up in ether. The solution was extracted successively with saturated sodium bicarbonate solution and saturated citric acid solution. The combined citric phases were alkalinized with 4 N sodium hydroxide, and extracted with ethyl acetate. The latter solution was dried over sodium sulphate and evaporated under reduced pressure. A light yellow oil was obtained and purified by flash chromatography on silicagel using chloroform as eluent (64%). Deprotection was performed by dissolving this derivative (2.65 mmol, 0.96 g) in trifluoroacetic acid (TFA) (5 g). It was stirred for 1.5 hours at room temperature. Then the TFA was evaporated and dry methanol was added and evaporated several times to remove traces of the acid. Addition of dry ether gave a crystalline product, which was filtered and dried (90% yield; M.p.: 97–98° C.). After coupling this compound with N-benzyloxycarbonylglycine and N-benzyloxycarbonyl-(S)-phenylalanine, the protected compounds were obtained. N-Benzyloxycarbonylglycine or N-benzyloxycarbonyl-(S)-phenylalanine (2.65 mmol) was dissolved in tetrahydrofuran (10 ml). After the addition of N-methylmorpholine (2.65 mmol, 0.27 g) the solution was cooled to −15° C. and isobutyl chloroformate (2.65 mmol, 0.36 g) was added. After 1 hour, a simultaneously prepared solution of methyl (S,S)-3-aza-2-benzyl-4-(2-pyrrolidinyl) butaboate trifluoroacetate (2.65 mmol, 1.00 g) in tetrahydrofuran (10 ml) was treated with N-methylmorpholine (2.80 mmol, 0.38 g) and added to the stirring mixed anhydride solution. This mixture was kept for 3 hours at room temperature. The solvent was removed under reduced pressure, the residue was taken up in ethyl acetate and washed with 5% citric acid solution (2×), water, 5% sodium bicarbonate solution (2×) and brine. After drying the organic layer over sodium sulphate and evaporating the solvent a yellow oil was obtained. The products were purified by column chromatography on silicagel with petroleumether:dichloromethane:ethyl acetate by gradient elution. [Glycine analogue: 60%; Phenylalanine analogue: 70%].

Deprotection of these compounds was done by hydrogenolysis. The protected compound (1.60 mmol) was dissolved in dry methanol (15 ml). After displacing the air with nitrogen, palladium-on-charcoal 10% (0,40 g) was added. Again nitrogen was blown over the solution before introducing the hydrogen. The reaction was stopped when no precipitation of barium carbonate could be detected in the barium hydroxide solution. After displacing the remaining gas by nitrogen, the palladium was removed on a celite filter and washed with methanol (3×5 ml). The filtrate was evaporated under reduced pressure and the remaining oil was dried over phosphor pentoxide. The title compounds were obtained as oils [Glycine analogue: 90%; Phenylalanine analogue: 95%].

Example 2

Evaluation of Inhibitory Activity

The inhibitory activity of some of the compounds as synthesized in Example 1 in vitro was determined by evaluating the protease activity of DPPIV in the presence of the compounds of the invention.

All enzymatic reactions were carried out in 50 mM Tris.HCl buffer pH 8.3 at 37° C. with Gly-Pro-4-Me-2-naphtylamine.HCl as substrate. One activity unit is defined as the amount of enzyme which catalyzes the conversion of 1 micromole of substrate per minute at 37° C. All experiments were carried out with the same stock solution of DPPIV containing 1.8 units/ml. The enzyme was diluted (usually 1/200 or 1/500) in reaction buffer immediately before the experiment to a suitable concentration so as not to consume more that 10% of the substrate during the incubation period.

b) Determination of $IC_{50}$ values

Inhibitor solutions were made in DMSO at various concentrations ranging between 50 and 0.01 mM. Five microliter of the inhibitor solution (or DMSO for the control experiment) was added to 40 microliter of DPPIV in reaction buffer and incubated at room temperature during 1 hour. The remaining activity was determined by adding 5 microliter of a 1 mM solution of Gly-Pro-4-Me-2-naphtylamine.HCl. The reaction mixture containing enzyme, substrate and inhibitor was incubated for 20 min at 37° C. The reaction was stopped by addition of 0.5 ml 100 mM citrate pH 4.0. The fluorescence of the sample was measured within 2 h after quenching. The measurements were done in duplicate and corrected for background fluorescence using a blanc with exactly the same composition except that the citrate solution was added before the substrate. The $IC_{50}$ value is defined as the inhibitor concentration which causes a 50% decrease in fluorescence.

c) Kinetic measurements

The kinetics of inactivation were measured by adding an appropriate concentration of inhibitor (0.1 or 0.5 mM) to 0.5 ml of enzyme in reaction buffer at 37° C. and determining the activity at various time points after mixing. To achieve this, 25 microliter samples were withdrawn and diluted 2-fold in 2 mM Gly-Pro-4-Me-2-naphtylamine.HCl. The reaction was quenched with citrate after 10 to 15 min and the fluorescence was determined. The dilution in an excess of substrate reduced the velocity of inhibitor binding by a factor of 20. The decrease in fluorescence with time was fitted with the equation of a monoexponential decay yielding the pseudo-first order rate constant for binding ($k_{obs}$) in the exponent. The second order rate constant ($k_+$) was calculated as follows: $k_+ = k_{obs}/[I]_o$ where $[I]_o$ is the concentration of inhibitor in the incubation mixture.

d) Stability

Phosphonate esters form a covalent adduct with the active site serine, analogous to the well documented acylated enzyme intermediate which is formed when substrate is cleaved by serine proteases. The phosphorylated enzyme is expected to hydrolyze slowly by action of solvent or nucleophilic groups on the enzyme. A stable adduct results in stoichiometric and irreversible inhibition of DPPIV without consumption of the inhibitor.

The stability of the adduct was determined as follows. DPPIV was incubated with 0.5 mM inhibitor (or an equivalent volume of DMSO for the control experiment) in 1 ml reaction buffer for 1 hour at 37° C., resulting in complete inhibition of the enzyme. Excess inhibitor was removed by gel filtration on a PD 10 column (Pharmacia Biotech, Uppsala, Sweden) previously equilibrated with 50 mM Tris.HCl buffer, pH 8.3. At regular time intervals the activity of the adduct was compared with the control sample which remained active for at least one month at 37° C. After 4 weeks, only a fraction of the activity was regained (about 10%) with the inhibitors mentioned in the table.

The following table lists the results of the above three experiments. Compounds marked with an asterisk (*) were racemic mixtures of diastereoisomers. The other compounds were separated into one inhibitory and one inactive diastereoisomer. The data in the table apply to the inhibitory diastereoisomer.

| Inhibitor | $IC_{50}$ (mM) | $K_+$ $(M^{-1} \cdot s^{-1})$ | stability of the adduct at room temperature |
|---|---|---|---|
| Pro-Pro$^P$-(OPh)$_2$* | 0.1 | 37 | >3 weeks |
| Phe-Pro$^P$-(OPh)$_2$ | 0.07 | 36 | >3 weeks |
| Ile-Pro-$^P$-(OPh)$_2$* | 0.35 | 2.3 | >3 weeks |
| O-tbutyl-Tyr-Pro$^P$-(OPh)$_2$ | 1.0 | 0.5 | |
| pF-Phe-Pro$^P$-(OPh)$_2$ | 0.1 | 40 | >4 weeks |
| Cyclohexylalanine-Pro$^P$-(OPh)$_2$ | 0.06 | 57 | >4 weeks |
| Ala-Pro-(OPh)$_2$* | 2 | 0.7 | >4 weeks |
| Ala-Pro$^P$-(OPh)$_2$* | 0.5 | 1.7 | >4 weeks |
| 1-naphthyl-alanine-Pro$^P$-(OPh)$_2$ | 0.3 | 2.3 | >4 weeks | d) Stability of selected DPPIV inhibitors in the reaction medium and in human citrated plasma To determine the functional stability of the inhibitors in the reaction medium, a 10 mM stock solution in DMSO was diluted 50-fold in 50 mM TRIS buffer pH 8.3 and incubated at 37° C. To determine the functional stability in plasma, a 50 mM stock solution in DMSO was diluted 50-fold in fresh or freshly frozen citrated plasma from a healthy donor and incubated at 37° C. At specific time intervals an aliquot was withdrawn, added to an equal volume of DPPIV diluted in buffer or to an equal volume of plasma and the kinetics of inactivation were determined as described under b). The reduction in observed pseudo-first order rate constant is a measure for the amount of functional inhibitor lost during the incubation and allowed to estimate the half-life of the inhibitors in buffer and plasma. The following table lists the results.

| Inhibitor | t½ in buffer (h) | t½ in plasma (h) |
|---|---|---|
| (S)-Pro-(S,R)-Pro$^P$(OPh)$_2$ | 3.5 ± 0.1 | 4.1 ± 0.3 |
| (S)-Phe-(R)-Pro$^P$(OPh)$_2$ | 6 ± 1 | 0.7 ± 0.1 |
| (S)-Ile-(R)-Pro$^P$(OPh)$_2$ | 10 ± 5 | 1.4 ± 0.9 |
| (S)-Arg-(S,R)-Pro$^P$(OPh)$_2$ | 2.6 ± 0.3 | 1.9 ± 0.2 |
| (S)-pF-Phe-(R)-Pro$^P$(OPh)$_2$ | 8.9 ± 0.1 | 0.7 ± 0.1 |
| (S)-Cyclohexylala-(R)-Pro$^P$(OPh)$_2$ | 4.5 ± 0.8 | 0.3 ± 0.1 |

Example 3

Effect of DPPIV Inhibitors on Recall Antigen Response of Human Lymphocytes

Synthetic inhibitors of DPP IV may modulate inadequate immune responses. As an example the effect of 2 of the products of the present invention on the recall antigen response in comparison to their effect on a mitogen induced stimulation of human lymphocytes was determined in a semi in vivo experiment.

a) Isolation of the CD8$^-$ fraction of human peripheral blood mononuclear cells (PBMC)

Human PBMC were isolated from EDTA anti-coagulated blood from healthy donors by density gradient centrifugation on Ficoll-Paque (Pharmacia, Uppsala, Sweden) as described elsewhere (Boyum A, 1968, Scand. J. Clin. Lab. Invest. 21, 77), and they were depleted of monocytes by a 2 h polystyrene adherence step (37° C.). To obtain CD8⁻ T cells, the monocyte-depleted PBMC were incubated with DYNABEADS M450 CD8 magnetic particles (Dynal, Oslo, Norway) according to the manufacturers™ instructions. The negatively selected cells were used for further investigations.

b) Cell cultures

Proliferation after recall antigen (Tetanus Toxoid) or mitogen (pokeweed mitogen) stimulation was assayed by [$^3$H] thymidine incorporation. Cells were cultured in RPMI at a final concentration of 1×10$^6$ cells/ml in the presence of 5% heat inactivated human AB serum. Tetanus Toxoid and Pokeweed mitogen were used in a final dilution of 1:200. Stock solutions of synthetic DPPIV inhibitors (250 mM) were made in DMSO; a final inhibitor concentration of 100 μmole/l was used during cell culture. Cells and inhibitor or control were incubated 1 h at 37° C. before the addition of stimuli and heat inactivated serum. Controls consisted of (1) solvent or (2) an inactive diastereoisomer of the synthetic inhibitors. Incubation was performed at 37° C. in a 5% $CO_2$ humidified atmosphere. After 4 days in 20 culture, the cells were pulsed with 0,4 μCi [$^3$H] thymidine/well (Amersham, UK), for 8 h. Cells were then harvested on glass filter paper and tritium incorporation was determined by liquid scintillation counting.

c) Results

Figure 2:
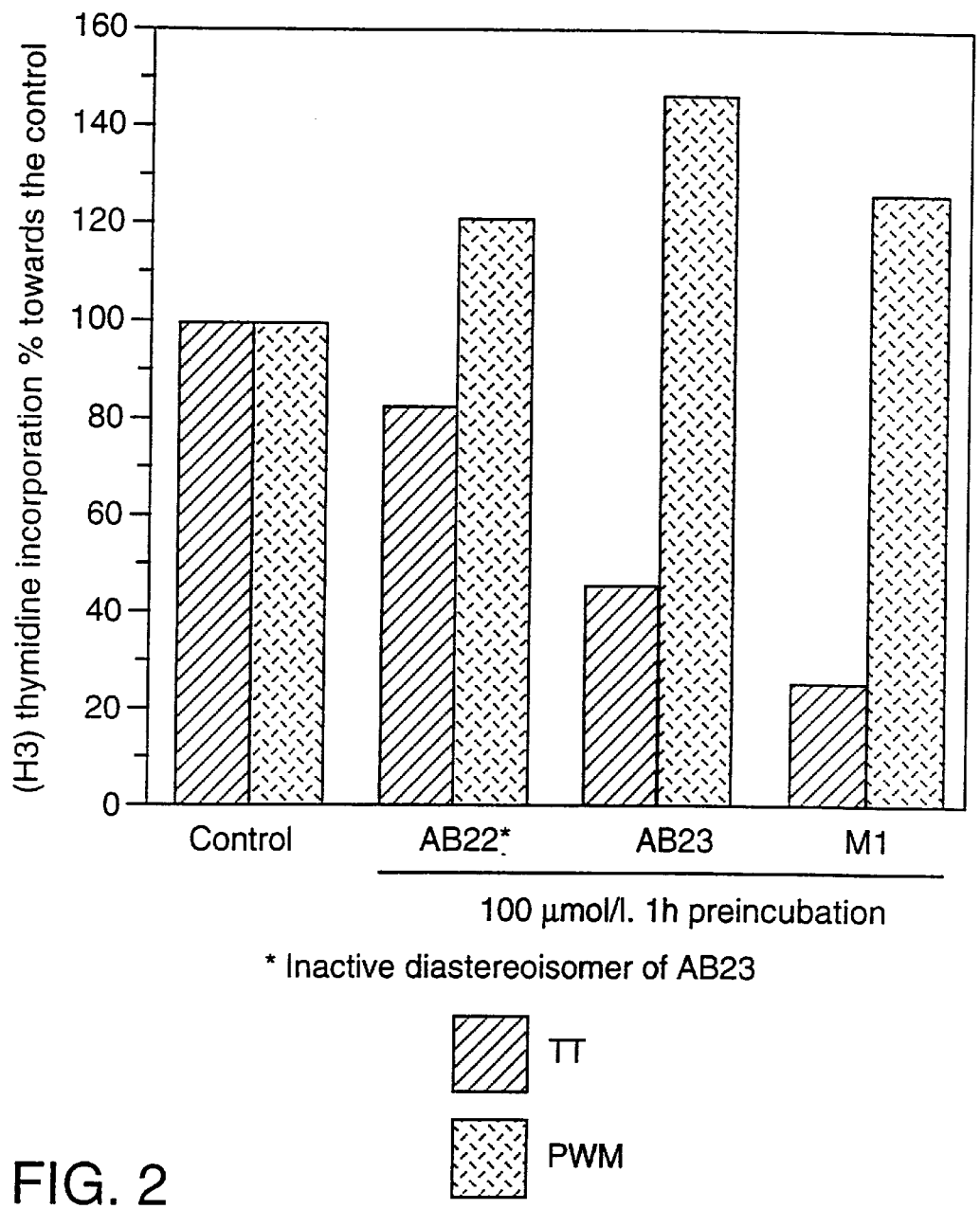
FIG. 2 shows the influence of DPPIV inhibitors on TT (tetanus toxoid) and PWM (pokeweed mitogen) simulation of human PBMC (Example 3)

The results of the lymphocyte stimulations are given in FIG. 2. the codes AB22, AB23, and M1 are used for the following products:

AB22: inactive diastereoisomer of Phe-Pro$^P$-(OPh)$_2$
AB23: Phe-Pro$^P$-(OPh)$_2$
M1: Pro-Pro$^P$-(OPh)$_2$ (racemic mixture)

The results show the influence of DPPIV inhibitors on recall antigen stimulation of human lymphocytes in vitro and may indicate their utility in the modulation of inadequate immune responses.

Example 4

Proteolytic Processing of Vasostatin by DPPIV and Inhibition Thereof

Chromogranin A (CGA), the best known member of the chromogranin/secretogranin family of acidic proteins contains highly conserved N- and C-terminal domains. The N-terminus contains a penultimate proline, a possible recognition site for DPPIV. The N-terminal fragment of chromogranin A (CGA1-76) has been named vasostatin I, reflecting its inhibitory effect on tension development in isolated blood vessels. Vasostatin has been shown to be produced as a family of peptides by the parathyroid cells. Recent evidence suggests that vasostatin plays an inhibitory role in calcium homeostasis via an inhibition of parathyroid hormone secretion at low plasma calcium.

In this experiment the processing of bovine vasostatin (CGA1-76) by purified DPPIV was studied in vitro as an illustration of the possible involvement of DPPIV in peptide metabolism.

Purified vasostatin (dried, 3 μg) was incubated during 44 hours at 37° C. with or without DPPIV (17 μg corresponding to 600 mU) in Tris 2 mM pH 8.0 in a final volume of 50 μl. After incubation, the samples were applied onto a YMC EPLC column (ODS 5 μm, 150×2 mm, 300 Å). The elution conditions consisted of a linear gradient of 100% buffer A (H20 containing 0.1% TFA) to 65% buffer B (acetonitrile containing 0.1% TFA) at a flow rate of 0.3 ml/min. UV detection was performed at 214 nm. The peptide containing fractions were subjected to electrospray/mass spectrometry to measure the relative molecular masses (Mr).

The Mr obtained were as follows: vasostatin incubated without DPPIV: 8583.9 vasostatin incubated with DPPIV: 8373.7 This Mr of the processed peptide corresponds to vasostatin 3-76 and proves the release of the N-terminal Leu-Pro (MR 113.1 for Leu and 97.1 for Pro respectively) from the parental peptide.

Addition of the inhibitor Pro-Pro$^P$-(OPh)$_2$ led to a substantial decrease in the enzyme activity of DPPIV.

Example 5

Purification of Dipeptidyl Peptidase IV (CD26, DPPIV) by Means of Immobilized Adenosine Deaminase The high specific DPP IV activity in prostasomes (Vanhoof et al., 1992) makes them a suitable source for the purification of the native DPP IV/CD26. Prostasomes are prostate-derived organelles which occur freely in human seminal plasma. The purification method is based on the fact that DPPIV binds adenosine deaminase (ADA).

a) Materials

The columns, chromatography media, and Low Molecular Weight Electrophoresis Calibration markers were obtained from Pharmacia Fine Chemicals, Uppsala, Sweden. The mini-PROTEAN®II cell and the 'Broad range SDS-PAGE Molecular Weight Standards' from Bio-Rad (Richmond, Calif., USA) were used. Gly-Pro-4-Me-2-NA, Ala-4-Me-2-NA and adenosine deaminase (ADA) from Calf intestinal Mucosa were obtained from Sigma Chemical Co, St.Louis, Mo., USA. All buffers for chromatography were filtered (0.22 μm) before use. Colorimetry was performed on an HP UV/VIS spectrophotometer 8450, Hewlett Packard, USA. Chromatography was carried out on a Waters 650 Advanced Protein Purification System, Millipore Co., Milford, Mass., USA. Fluorometric measurements were done on a model RF5000 fluorometer (Shimadzu Corp., Tokyo, Japan).

b) Procedures

Enzyme Assays

Dipeptidyl peptidase IV activity was determined as described previously. (Scharpé et al. 1988) Hydrolysis of L-Ala-4-Me-2-NA (2 mmole/l) in 60 mmole/l phosphate buffer, pH 7.4, was chosen for the determination of aminopeptidase M (mAAP, EC 3.4.11.9) activity. One unit of enzyme activity was defined as the amount of enzyme catalyzing the formation of 1 μmole of assay-product/min under assay conditions.

Protein Determination

The protein concentration was determined by the micro assay procedure of the Bradford method (Bradford, 1976), based on Coomassie Brilliant Blue G-250. BSA was used as the standard. Interfering substances were blank corrected.

Isolaton of Human Prostasomes

Prostasomes were isolated from human seminal plasma as follows: seminal plasma was centrifuged at 900 g during 10 minutes in a MSE HI-spin 21 centrifuge (MSE Scientific Instruments, Sussex, UK), to pellet the spermatozoa. The resulting supernatant was centrifuged at 105 000 g during 60 min (Beckman Ultracentrifuge model L3-50, Beckman Instruments, München, Germany) to obtain the prostasomes and the seminal fluid. The prostasomes were washed twice in 20 mmole/Tris-HCl, pH 7.4. Afterwards they were solubilized in the same buffer containing 1% (v/v) Triton X-100 and centrifuged at 40 000 g (10 min) to clarity the solution.

Immobilization of Adenosing Deaminase (ADA)

ADA was immobilized onto cyanogen bromide activated Sepharose 4B following the instructions of Pharmacia, Uppsala, Sweden. 5 mg ADA was used per ml Sepharose gel. ADA solution was dialyzed extensively against coupling buffer (NaHCO$_3$ 0.1 M, NaCl 0.5 M, pH 8.3) and added to CN-Br-activated Sepharose 4B gel after washing the gel during 15 min with HCl (1 mM) and equilibration with coupling buffer. After rotating during 2 hours at room temperature in an end over end mixer, the gel was washed with coupling buffer. The remaining active groups were blocked by incubation with Tris-HCl 0.1 M, pH 8.0 overnight at 40° C., while rotating. The ADA-Sepharose 4B gel was washed with 3 cycles of acetate buffer (CH$_3$COONa 0.1 M, NaCl 0.5 M, pH 4) followed by Tris-HCl buffer (Tris 0.1 M, NaCl 0.5 M, pH 8.0). Storage at 4° C. in Tris-HCl 20 mM, pH 7.4 containing 0.02% thiomersal was possible for at least 18 months.

Purification Procedure

Step 1: Anion exchange chromatography on DEAE-Sepharose® Fast Flow

The prostasome extract was subjected to ion-exchange chromatography on a column of DEAE-Sepharose Fast Flow (2.6×10 cm) equilibrated with 20 mM Tris-HCl, 70 mM NaCl, 0.1% (v/v) Triton X-100, pH 7.4, at a flow rate or 2 ml/min. The column was eluted with 300 ml of a linear gradient of NaCl (70–350 mM) in the same buffer at a flow rate of 3 ml/min.

Step 2: Affinity chromatography onto ADA-Sepharose 4B

The active fractions of the anion exchange column were pooled, dialyzed against 0 mm Tris-HCl pH 8.0, containing 150 mM Nacl and 0.1% Triton X-100 and applied onto the ADA-Sepharose (1.5×3.5 cm) column equlibrated with the same buffer (flow rate 0.35 ml/m). After washing the column with 5 column volumes equilibration buffer and subsequently with an equal amount of 50 mM Tris-HCl, pH 7.4 containing 500 mM NaCl and 0.1% Triton-X 100, the adsorbed enzymes was eluted with 2 mmole/l Tris-HCl pH 8.0, containing 0.1% Triton X-100. Column washing and elution of the enzyme was carried out at a flow rate of 1 ml/min.

The results of the purification are summarized below.

|  | Activity mU | Yield % |
|---|---|---|
| Prostasome extract | 17900 | 100 |
| DEAE-Sepharose | 2500 | 70 |
| ADA-Sepharose | 6900 | 40 |

This two-step purification procedure separates aminopeptidase M and DPP IV, which behave very similar during most classical chromatography procedures including anion exchange, gelfiltration and metal-chelating affinity chromatography. The DPP IV/CD26 preparation obtained via this scheme was homogeneous on silver-stained SDS-Page. FIG. 1 shows the SDS-page from the purified DPP IV and aminopeptidase M preparation obtained from human prostasomes. The Mr estimated from SDS-Page were 114 000 for DPP IV and 129 500 for mAPP. Purified DPP IV was stored at −70° C. The loss of enzyme activity after 1 year is less than 10%. At room temperature the enzyme preparation is stable for at least 3 weeks.

Example 6

In vivo inhibition of DPPIV Pro-Pro$^P$-(OPh)$_2$ (AB 3)

In order to test the effect of the inhibitors in vivo rabbits were injected with the inhibitor and their DPPIV activity was tested using Gly-Pro-4-Methoxy-2-naphthylamide as the substrate.

4 Rabbits received a single 5 ml intravenous-(ear vein) injection of physiological saline cobtaining 0 (control), 1 mg, 5 mg and 10 mg AB 3, respectively. Blood samples were taken from the central ear artery 5 min before injection and at different points of time, directly after the injection, after 4 hrs and after 1, 2, 3, 6 and 13 days.

Counts of white and red blood cells and platelets, serum DPPIV activity and serum bilirubin, GOT, GPT, GT, LDH, creatinine, Na, K, CK and urea were evaluated. No differences were seen in cell counts or in the biochemical parameters except for the DPPIV enzyme activity. The animal receiving 10 mg AB3 died after 11 days although at day 6 the biochemical and hematological parameters were normal.

Figure 3:
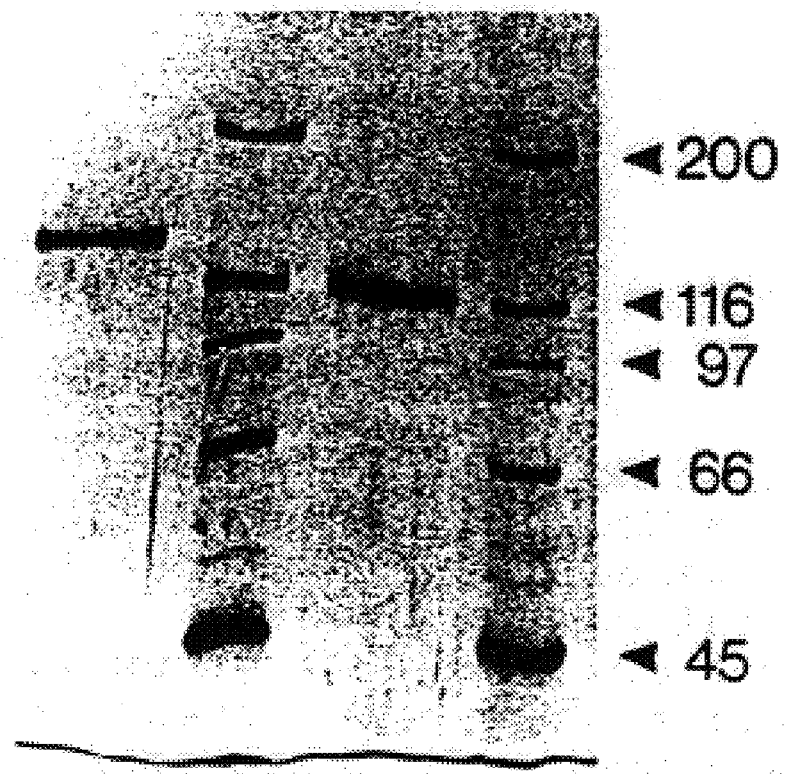
FIG. 3 shows a silver stained SDS-PAGE gel showing purified DPPIV in lane 3 in comparison with molecular weight markers in lanes 2 and 4, and purified aminopeptidase M in lane 1 (Example 5)
Figure 4:
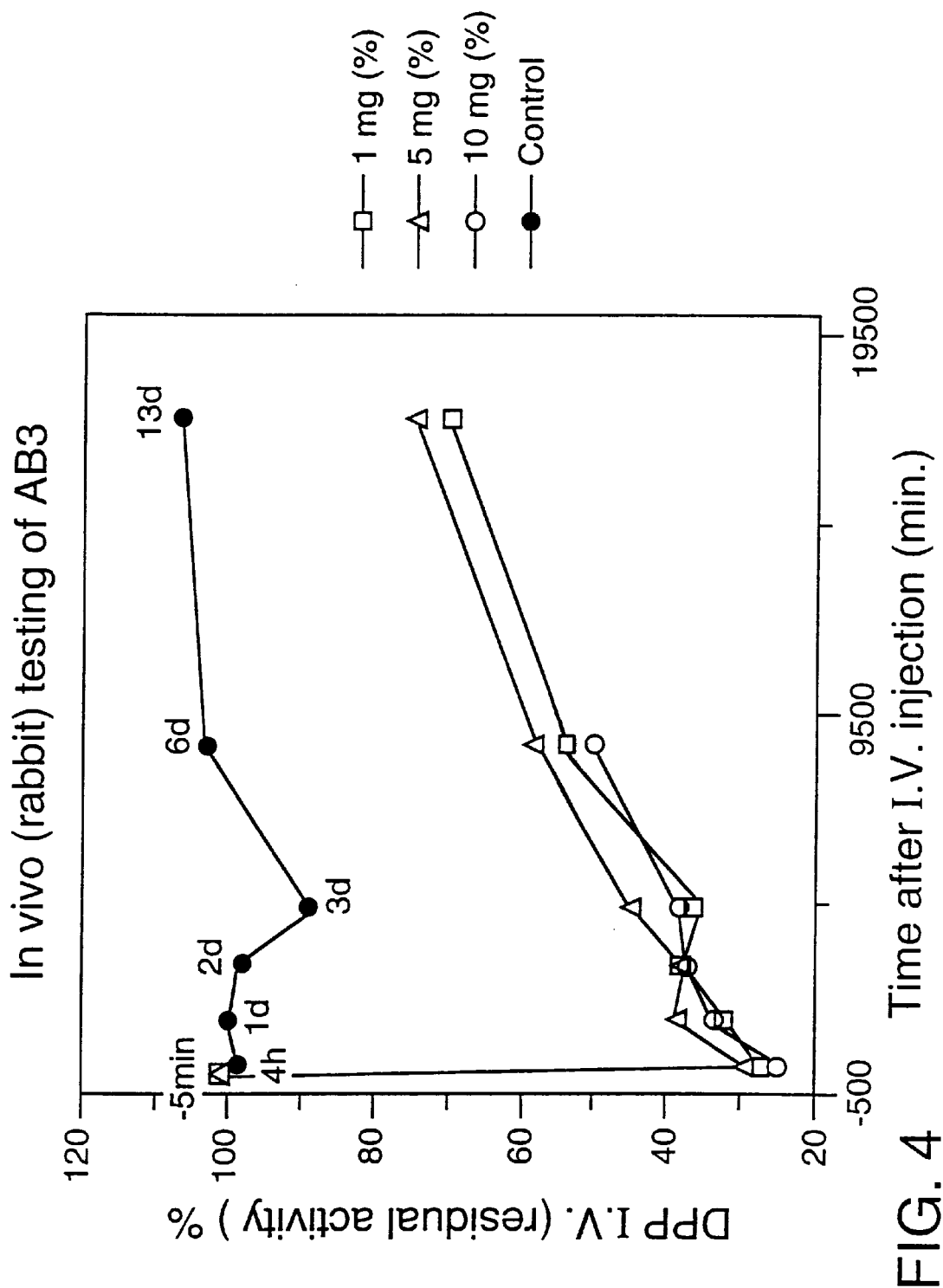
FIG. 4 shows an illustration of the in vivo testing of rabbits of the compound (AB3) (Example 6)

FIG. 3 shows serum DPPIV activity expressed as % of serun DPPIV activity 5 min before injection.

Example 7

Purification of PEP

Prolyl endopeptidase was isolated and purified to homogeneity from human peripheral blood mononuclear cells. Up till now this source was not yet used for PEP isolation.

a) Materials

N-benzyloxycarbonyl-glycyl-prolyl-4-methyl coumarinyl-7-amide (Z-Gly-Pro-MCA), and 7-amino-4-methylcoumarine were obtained from Bachem Feinchemikalien AG, bubendorf, Switzerland. N-benzyloxycarbonyl-prolyl-prolinal (Z-Pro-Prolinal) and N-benzyloxycarbonyl-thioprolyl-thioprolinal (Z-thipro-thioprolinal) were kindly provided by Prof. T. Yoshimoto (University of Nagasaki, Nagasaki, Japan) and Dr. K. Kato (Yakult Co., Tokyo, Japan), respectively. Ethylenediaminetetra-acetate (EDTA), dithiothreitol (DTT), di-isopropylfluorophosphate (DFP), phenylmethylsulphanylfluoride (PMSF), amastatin, bestatin, ornithine decarboxylase, ubiquitin, α1-antitrypsin, α1-casein, albumin and antibodies towards albumin were purchased from Sigma Co., St. Louis, USA. All other reagents were of analytical grade from E. Merck, Darmstadt, Germany. All chromatography materials were obtained from Pharmacia, Uppsala, Sweden. The materials used for electrophoresis were purchased from Bio-Rad, Richmond, USA. The complete equipment for HPLC was from Gilson, Paris, France. The system for amino acid sequencing, Applied Biosystems type 470 A, was obtained from Applied Biosystems, Warrington, UK b) Isolation of Sononuclear Cells Buffy coats were prepared from units of whole blood collected from blood bank donors using standard procedures. The buffy coats were diluted with an identical volume of 0.9 (w/v) NaCl containing 0.3% (w/v) tri-sodium-citrate. This solution was further diluted with equal parts of Plasmasteril (Fresenius, Bad Homburg, Gerany), and the mixture was left for 1–2 h at room temperature. 5 ml of cell suspension was layered upon 3 ml of Lymphoprep (Nycomed, Oslo, Norway) and centrifuges at 800×g for 20 min at 20° C. The mononuclear cells were concentrated on the gradient layer and aspirated using a Pasteur pipette. The mononuclear cell layer was washed with phosphate buffered saline (NaCl 8.0 g/l, KCl0.2 g/l, KH$_2$PO$_4$ 0.2 g/l, Na$_2$HPO$_4$ 1.15 g/l; pH 7.4; PBS) containing 0.3% (w/v) tri-sodium-citrate and subsequently centrifuged at 700×g for 10 min whereafter the pellet is redissolved in PBS containing 0.3% (w/v) tri-sodium-citrate. This procedure was repeated twice. The final pellet was stored at −80° C.

c) Purification of Prolyl Oligopeptidase from Mononuclear Cells

Mononuclear blood cells were disrupted by freezing and thawing (−80° C. and +20° C.) followed by shearing in a Potter-Elvehjem at 500 rpm (2×15 sec). All further procedures were performed at 4° C. except otherwise stated. The intact cells were removed by centrifugation at 29 000×g for 60 min. Under constant stirring cooled acetone (−15° C.) was slowly added to the supernatant to a final concentration of 32%. The precipitate was removed by centrifugation in closed polycarbonate tubes at 4 500×g for 20 min. The supernatant was treated with ammonium sulphate. Solid ammonium sulphate was added slowly and under constant stirring to a final concentration of 65% (w/v). The mixture was centrifuged at 4 500×g for 20 min. The precipitated proteins accumulated at the interphase between the acetone layer and the ammonium sulphate solution. The liquid phases were removed and the precipitate was extracted repeatedly with a small amount of Tris-HCl 20 mM pH 7.5 containing 1 mM EDTA, 1 mM $NaN_3$ and 1 mM DTT (buffer A). After centrifugation at 4 500×g for 10 min the supernatant was dialyzed overnight against buffer A. Before chromatography, the dialysate was centrifuged at 15 000×g for 30 min. Step 1: the supernatant was loaded on a DEAE-sepharose fast flow column that was washed with buffer A. The flow used for loading was 1 ml/min and increased to 2 ml/min as the gradient is started. The proteins are desorbed using a linear gradient 0 to 0.25 M NaCl in buffer A. Step 2: The active fractions from the previous step are combined and diluted 5 times with buffer A and applied onto a Q-Sepharose HiLoad column that was equilibrated with buffer A. The flow conditions are identical as for the previous step. The proteins are eluted with a linear NaCl Gradient between 0–0.4 M in buffer A. Step 3: The active fractions are combined and saturated with solid ammonium sulphate to 25% (w/v). The enzyme solution was then applied on a Phenyl Sepharose CL-6B column that was previously equilibrated with buffer A containing 25% (w/v) amonium phase. The flow rate was 0.35 ml/min during loading and elution. The proteins were eluted using a linear gradient of ethylene glycol (50% (w/v) in buffer A). The active fractions were collected and the ethylene glycol was removed by gel filtration on a sephadex G-25 column, which was washed with buffer A. Step 4: Finally the enzyme was passed through a column with immobilized anti-albumin antibodies at a flow rate of 0.1 ml/min.

c) Characterization

Amino Acid Sequencing

Purified enzyme was subjected to partial amino hydrolysis in 1% (v/v) formic acid at 110° C. for 4 hours. The peptides generated were separated on HPLC using a linear gradient between 10 and 75% (v/v) acetonitrile in $H_2O$ containing 0.85% (v/v) TFA. Separate peaks were vacuum dried in a Savant and stored until application in the automated sequencer at −20° C. One of the most abundant peptides was then chosen for sequencing. The peptide was dissolved in 10% (v/v) TFA and applied onto a polybrene membrane and subsequently subjected to the Edman degradation.

Protein Determination

Protein concentrations were measured with Coomassie Brilliant Blue G-250 according to Bradford with BSA as the standard (Bradford, Anal. Biochem. 72, 248–254 (1976)).

Enzyme Assay

PEP measurement was carried out as previously described (Goossens et al., Eur. J. Chem. Clin. Biochem. 30, 235–238 (1992)) with the following modifications. Incubations lasted for 20 min at 37° C. and the substrate stock solution contained 5.7 mM Z-Gly-Pro-MCA dissolved in DMSO. 10 $\mu$l sample was added to 100 $\mu$l K-phosphate buffer (K-phosphate 100 mM, pH 7.5, EDTA 1 mM, Dtt 1 mM, NaN3 1 mM), whereafter the substrate is added. The reaction is stopped by the addition of 500 $\mu$l acetic acid (1.5 M acetic acid). The fluorescence is measured at $\lambda$ex 370 nm and $\lambda$em 440 nm, slitwidth 1.5 nm on a Shimadzu RF-5000.

Apparent $K_m$ constants were determined by a direct linear plot using concentrations ranging from $K_m/10$ to $K_m \times 2$.

Determination of pH Optimum

The stability of PEP with respect to pH was examined by preincubating the enzyme for 150 min at 4° C. at different pH values ranging from 3 to 12 after which the reaction was started under standard enzyme assay conditions. The pH optimum was determined with the standard assay using Tris-acetate buffers. We investigated the pH dependence at pH values ranging from 6.2 tot 9.4.

Determination of Optimal Temperature

The stability of PEP as a function of temperature was tested by preincubating the cytosol for 20 min at different temperatures, followed by the measurement of the residual activity at 37° C. The optimum was determined by the standard enzyme assay except for the change in incubation temperature, which varied from 25 to 47° C.

Determination of the Iso-eletric Point

The iso-electric point was estimated by iso-electric focusing in free solution on an $RF_3$ (Protein Technologies, Woburn, USA). The ampholytes, range pH 4–7 (from the same supplier), were diluted in 20 mM Tris-HCl, pH 7.5, containing 1 mM EDTA, 1 mM $NaN_3$, and 1 mM DTT and 40% ethylene glycol. We prefocused the ampholytes for 60 min at 1600 V, after which 6 ml of the crude, dialyzed (against Tris-HCl 20 mM, pH 7.5) cytosol was injected in the apparatus. The temperature never exceeded 12° C. The run was further accomplished by focusing the protein solution for 120 min at 1000 V and finally for 30 min at 500 V. All fractions were collected and both the pH and the enzymatic activity were determined in every fraction.

Affinity for Concanavalin A 5 ml of crude dialyzed cytosol were applied on a concanavalin A column previously equilibrated with 20 mM Tris-HCl, pH 7.5, containing 1 M NaCl. Elution was performed with the same buffer to which 400 mM methyl-$\alpha$-D-mannoside had been added.

SDS-PAGE electrophoresis

Polyacrylamide gel electrophoresis was performed at 200 V in 10% gels according to Laemmli. 10% gels were manually prepared on the day of the electrophoresis, following the protocol of Bio-Rad. The running buffer consists of SDS (5 g/l), Glycine (72 g/l) and Tris (15 g/l). After the electrophoresis, the proteins were visualized using silver staining.

d) Results

Prolyl endopeptidase is a cytosolic enzyme since negligible activity is found in the pellet after disruption and centrifugation of the mononuclear blood cells. Additionally the enzyme elutes in one peak on both Sephacryl S-300 HR and S-100 HR, showing there is no adsorbtion to some subcellular particles and hence it is completely soluble. The specific activity of PEP in mononuclear cells, as in platelets, is 3.0 mU/mg which is high with respect to the other human tissues that were screened for activity (results no shown). The total activity found in mononuclear blood cells and platelets is high enough to mediate the level of prolyl oligopeptidase in human plasma. The tissue generating serum PEP is still unknown, but since PEP is found throughout the whole body many tissues may participate.

The enzyme is stable in the pH-range 6–9 and up to 43° C. The relative molecular mass of native PEP estimated by gelfiltration on a Sephacryl S-100 HR was 68 kDa. This was confirmed by SDS-PAGE analysis of the purified enzyme where one band at 76 kDa was visualized after silver staining. The comparable molecular size of native and denatured enzyme indicate the enzyme exists as a monomer. The calculated molecular mass of 80 745 of the enzyme from its amino acid composition further supports this result. The iso-electric point was determined by isoelectric-focusing in free solution and was 4.8. The enzyme bears no mannopyranosyl moiety since there is no affinity for concanavaline A. The different chromatographic separations, based on molecular weight, hydrophobicity and charge respectively, all reveal one peak of enzymatic activity indicating we are dealing with a single enzyme capable of degrading the synthetic substrate Z-Gly-Pro-AMC. Its molecular weight rules out any interference by angiotensinase C, and the addition of EDTA prevents NEP (neutral endopeptidase) to participate in the metabolization of peptides. A variation of this purification procedure was also used to purify PEP from human thrombocytes (platelets).

Example 8

In vitro Inhibition of PEP

It is generally accepted that the blood pressure is under control by the renin angiotensin system. The key enzymes are renin and angiotensin converting enzyme. However, it has been suggested by Goldfarb (Goldfarb, D. & Novick, A. Urology 43, 572–583 (1994)) and others that other enzymes are involved in the management of the blood pressure. One of which is prolyl oligopeptidase. This enzyme converts angiotensin II and angiotensin I to angiotensin (1–7), degrades bradykinin and antidiuretic hormone.

In order to test the inhibition of prolyl oligopeptidase by the compounds of the invention the inhibitors (cfr. table) were preincubated with purified human platelet prolyl oligopeptidase in 100 µl buffer (100 mM $K_2HPO_4$-$KH_2PO_4$, pH 7.5, 1 mM EDTA, 1 mM $NaN_3$) at 37° C. during 20 min. The remaining activity was determined by adding 5 µl substrate (Z-Gly-Pro-AMC, 5.6 mM) and measurement of the fluorescence at $\lambda_{ex}$370 nm, $\lambda_{em}$440 nm after a further 20 min incubation at 37° C. The inhibitors were dissolved in methanol and control experiments were performed to correct for the presence of the solvents used. The $IC_{50}$ value was derived from a plot, joining the residual activity and the dosis of the respective compounds (at least eight concentrations tested). The $K_i$ values were derived from a direct linear plot (Dixon-plot). The measurements were performed in triplicate and only those lines having a correlation coefficient of at least 0.95 were used for determination of the $K_i$ value.

|  | $IC_{50}$ (µM) | $K_i$ (µM) |
| --- | --- | --- |
| Z-Phe-azetidine | 30 | — |
| Z-Pro-azetidine | 3.0 | 2.5 |
| Z-thiopro-azetidine | 1.8 | 5.0 |
| Z-Pro-3-fluoropyrrolidine | 0.45 | 0.10 |

Example 9

PEP Catalyzed Degradation of Proline Containing Peptides

Several peptides (cfr. table) were incubated with purified prolyl oligopeptidase. The compounds were dissolved in $H_2O$. The $IC_{50}$ value was determined as previously described apart from the preincubation which was deleted. In a parallel experiment, the peptides were incubated in the same buffer, in the presence of purified human prolyl oligopeptidase, during at least 30 min at 37° C. The general fragments were separated on HPLC. Addition of 1 µmol of Z-thioprolyl-thioprolinal to the incubation mixture of enzyme and peptides, completely prevented the hydrolysis of the testpeptides.

The conditions for HPLC were as follows: Vydac $C_{18}$ (2.1×150 mm) flow 200 µL/min, linear gradient from 0% acetonitril (0.75% TFA in $H_2O$) to 70% acetonitrile (in 0.75% TFA in $H_2O$) during 30 min. Detection of the fragments at 220 mm, 0.100 AUFS. The fragments were controlled by amino sequencing. This proved they were cleaved at a postproline peptide bond.

|  | $IC_{50}$ (µM) |
| --- | --- |
| Bradykinin | 7 |
| Angiotensin II | 25 |
| Angiotensin (1–7) | 750 |
| Substance P | 163 |

It could be demonstrated that purified prolyl oligopeptidase hydrolyses Factor X of the clotting cascade, which gives evidence for a role in hemostasis and thrombosis. Factor X (Sigma Co.) was incubated in phosphate buffer (same as supra) containing 1 mM DTT. The clotting factor was incubated alone as a control for autocatalysis, with prolyl oligopeptidase and with the enzyme in the presence of an inhibitor (1 µmol Z-thioprolyl-thioprolinal). These experiments present evidence that Factor X is hydrolysed by prolyl oligopeptidase, since autocatalysis was ruled out and addition of a specific inhibitor for the enzyme prevented the breakdown of the clotting factor.

Figure 5:
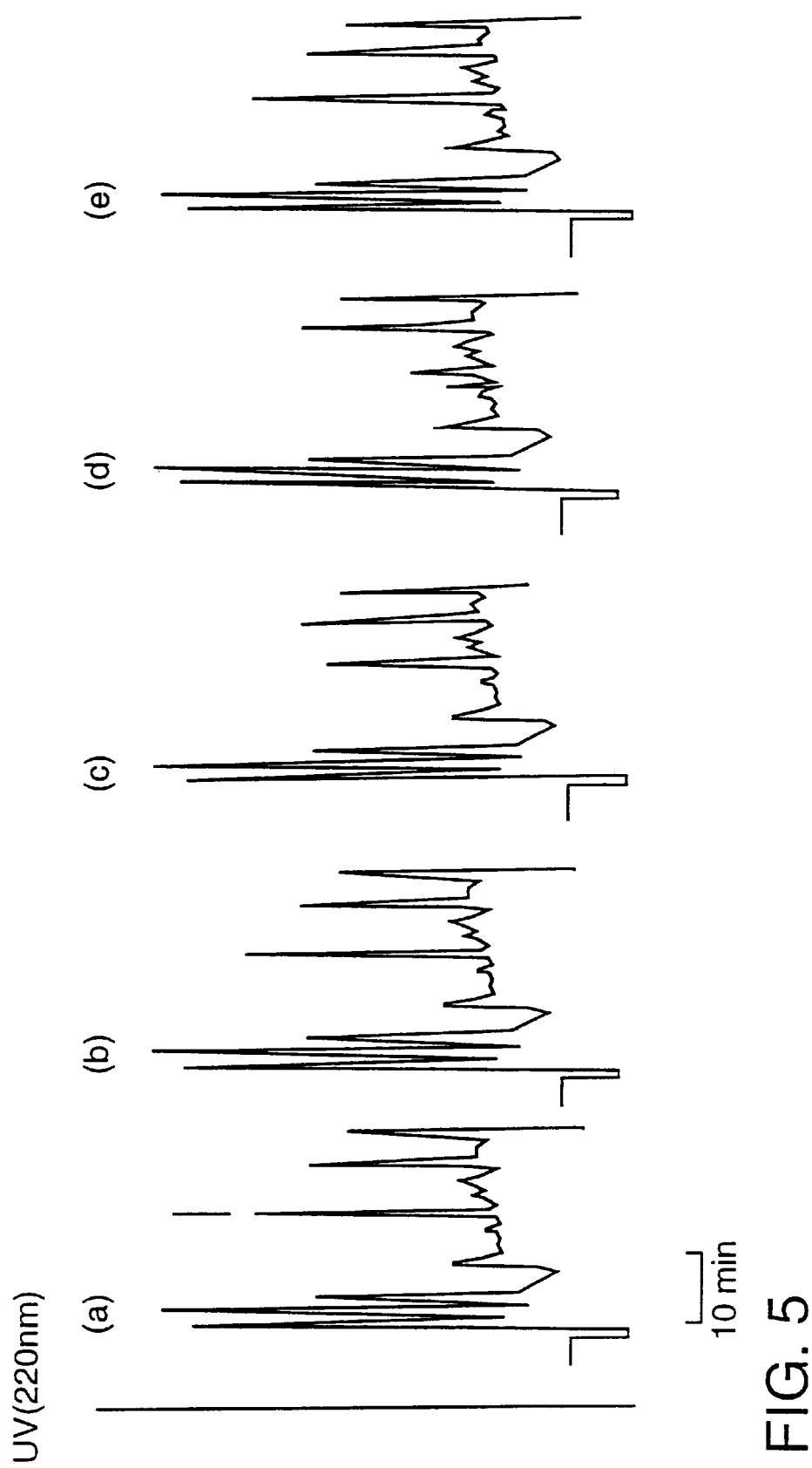
FIG. 5 shows an illustration of the hydrolysis of factor X by human platelet prolyl oligopeptidase (Example 9).

The EPLC pattern for factor X is shown in FIG. 5, which illustrates the effect of hydrolysis of Factor X at 37° C. during 16 h unless otherwise stated. (a) is pure Factor X; (b) is prolyl aligopeptidase (PEP) in the presence of Z-thiopro-thioprolinal; (c) is Factor X and PEP incubated for 60 min; (d) is Factor X and PEP; and (e) is Factor X and PEP in the presence of Z-thiopro-thioprolinal.

We claim:

1. A compound having a modulating activity on serine proteases, the compound having the general formula:

Z-Xaa-Y' wherein

Z is absent or a protecting group;

Xaa is selected from the group consisting of: alanine, methionine, arginine, phenylalanine, aspartic acid, proline, asparagine, serine, cysteine, threonine, glycine, tyrosine, glutamic acid, tryptophan, glutamine, valine, isoleucine, lysine, leucine, L-thioproline, L-homoproline, L-1,2,3,4, tetrahydroisoquinoline-3-carboxylic acid (Tic), L-2,3-dihydroindol-2-carboxylic acid, L-naphthylglycine, L-phenylglycine, L-4-phenylproline, O-benzyl tyrseine, omega-Z lysine and omega-acetyl lysine; and Y' is a pyrrolidide of the general formula:

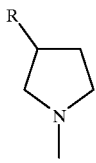
(II)

wherein R is a halogen atom; or pharmaceutically acceptable salts thereof.

2. The compound as claimed in claim 1 in which the compound is Z-Pro-3-fluoro-pyrrolidide.

3. The compound as claimed in claim 1 in which the compound is Ile-3-fluoro-pyrrolidide.

4. A method for inhibiting serine protease activity comprising administering an effective amount of a compound having the general formula:

Z-Xaa-Y' wherein

Z absent or a protecting group;

Xaa is selected from the group consisting of: alanine, methionine, arginine, phenylalanine, aspartic acid, proline, asparagine, serine, cysteine, threonine, glycine, tyrosine, glutamic acid, tryptophan, glutamine, valine, isoleucine, lysine, leucine, L-thioproline, L-homoproline, L-1,2,3,4, tetrahydroisoquinoline-3-carboxylic acid (Tic), L-2,3-dihydroindol-2-carboxylic acid, L-naphthylglycine, L-phenylglycine, L-4-phenylproline, O-benzyl tyrosine, omega-Z lysine and omega-acetyl lysine;

and Y' a pyrrolidide of the general formula:

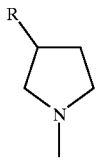
(II)

wherein R is a halogen atom; or pharmaceutically acceptable salts thereof.

* * * * *

UNITED STATES PATENT AND TRADEMARK OFFICE
CERTIFICATE OF CORRECTION

PATENT NO. : 6,090,786
DATED : July 18, 2000
INVENTOR(S) : Koen J. L. Augustyns et al.

It is certified that error appears in the above-identified patent and that said Letters Patent is hereby corrected as shown below:

Column 3 Line 6 "DPPTV" should read --DPPIV--.

Column 4 Line 26 delete "SUMMARY OF THE INVENTION".

Column 4 between Lines 29 and 30 insert --SUMMARY OF THE INVENTION--.

Column 6 Line 56 after "Pro-Pro$^P$-(Oph)$^{2}$" insert comma --,--.

Column 6 Line 59 "(OPH)$_2$" should read --(OPh)$_2$--.

Column 7 Line 35 "MeoH" should read --MeOH--.

Column 7 Line 40 "Bodaneki" should read --Bodanski--.

Column 7 Lines 42-43 "pentafluorophfenol" should read --pentafluorophenol--.

Column 9 Line 57 "substances(s)" should read --substance(s)--.

Column 10 Line 34 "5 A." should read --A.--

Column 10 Line 53 "intemediate" should read --intermediate--.

Column 11 Line 12 "CHCl3" should read --CHCl$_3$--.

Column 11 Line 59 "$^1$N-NMR" should read --$^1$H-NMR--.

UNITED STATES PATENT AND TRADEMARK OFFICE
CERTIFICATE OF CORRECTION

PATENT NO. : 6,090,786
DATED : July 18, 2000
INVENTOR(S) : Koen J. L. Augustyns et al.

It is certified that error appears in the above-identified patent and that said Letters Patent is hereby corrected as shown below:

Column 12 Line 67 "melting paint" should read --melting point--.

Column 13 Line 11 "(100)" should read --(100).

Column 13 Line 14 "35 yield" should read --yield--.

Column 13 Line 15 "phenaylalyl" should read --phenylalanyl--.

Column 13 Line 33 "phophonate" should read --phosphonate--.

Column 13 Line 58 "(m, 1H)" should read --(m, 2H)--.

Column 14 Line 2 "$^1$NMR" should read --$^1$H-NMR--.

Column 14 Line 7 "= - 80.0°" should read -- = 80.0°-- (delete minus).

Column 14 Line 13 before "15.5" insert -- = -- (equal sign).

Column 14 Line 45 "95-5))" should read --95-5)]--.

Column 15 Line 26 "1-N-" should read --1'[N--.

Column 15 Line 29 "2.66 mol) should read --2.66 mmol)--.

Column 16 Line 34 "dichioromethane" should read --dichloromethane--.

Column 17 Line 54 "of-the" should read --of the--.

UNITED STATES PATENT AND TRADEMARK OFFICE
CERTIFICATE OF CORRECTION

PATENT NO. : 6,090,786
DATED : July 18, 2000
INVENTOR(S) : Koen J. L. Augustyns et al.

It is certified that error appears in the above-identified patent and that said Letters Patent is hereby corrected as shown below:

Column 19 Line 20 "in 20 culture" should read --in culture--.

Column 19 Line 27 after "FIG. 2." delete "the" and insert --The--.

Column 19 Line 61 "EPLC" should read --HPLC--.

Column 20 Line 64 "to clarity" should read --to clarify--.

Column 21 Line 9 "40°" should read --4°--.

Column 21 Lines 21-22 "flow rate or" should read --flow rate of--.

Column 21 Line 27 "0 mm" should read --50 mM--.

Column 21 Line 28 "Nacl" should read --NaCl--.

Column 21 Line 43, under column entitled "Activity mU", "2500" should read --12500--.

Column 22 Line 15 "serun" should read --serum--.

Column 22 Line 45 "Sononuclear" should read --Mononuclear--.

Column 22 Line 51 "Gerany" should read --Germany--.

Column 23 Line 35 "amonium" should read --ammonium--.

UNITED STATES PATENT AND TRADEMARK OFFICE
CERTIFICATE OF CORRECTION

PATENT NO. : 6,090,786
DATED : July 18, 2000
INVENTOR(S) : Koen J. L. Augustyns et al.

It is certified that error appears in the above-identified patent and that said Letters Patent is hereby corrected as shown below:

Column 24 Line 21 "Iso-eletric" should read --Iso-electric--.

Column 27, last line, Claim 4, after "Z" insert --is--.

Signed and Sealed this

Seventeenth Day of April, 2001

Attest:

NICHOLAS P. GODICI

Attesting Officer    Acting Director of the United States Patent and Trademark Office